US009101342B2

(12) United States Patent
Saleh

(10) Patent No.: US 9,101,342 B2
(45) Date of Patent: Aug. 11, 2015

(54) SURGICAL RETRIEVAL APPARATUS AND METHOD WITH SEMI-RIGIDLY EXTENDABLE AND COLLAPSIBLE BASKET

(76) Inventor: Rafic Saleh, Aquadilla, PR (US)

(*) Notice: Subject to any disclaimer, the term of this patent is extended or adjusted under 35 U.S.C. 154(b) by 0 days.

(21) Appl. No.: 13/458,351

(22) Filed: Apr. 27, 2012

(65) Prior Publication Data

US 2013/0023895 A1 Jan. 24, 2013

Related U.S. Application Data

(63) Continuation-in-part of application No. 13/356,436, filed on Jan. 23, 2012, which is a continuation-in-part of application No. 13/189,041, filed on Jul. 22, 2011, now abandoned.

(51) Int. Cl.
*A61B 17/3205* (2006.01)
*A61B 10/02* (2006.01)
*A61B 10/04* (2006.01)
*A61B 17/221* (2006.01)
*B21F 45/00* (2006.01)
*A61B 17/00* (2006.01)

(52) U.S. Cl.
CPC ............... *A61B 10/02* (2013.01); *A61B 10/04* (2013.01); *A61B 17/221* (2013.01); *B21F 45/008* (2013.01); *A61B 2017/00287* (2013.01)

(58) Field of Classification Search
CPC ...... A61B 10/02; A61B 10/04; A61B 17/221; A61B 17/32056; A61B 2017/00287; A61B 17/00269; A61B 17/2212
USPC ................................ 606/113, 114, 127, 200
See application file for complete search history.

(56) References Cited

U.S. PATENT DOCUMENTS

| 3,791,387 | A | | 2/1974 | Itoh |
|---|---|---|---|---|
| 4,625,726 | A | * | 12/1986 | Duthoy .................. 606/127 |
| 5,190,542 | A | * | 3/1993 | Nakao et al. ............ 606/47 |
| 5,201,740 | A | | 4/1993 | Nakao et al. |
| 5,345,936 | A | * | 9/1994 | Pomeranz et al. ......... 600/374 |
| 5,486,182 | A | | 1/1996 | Nakao et al. |
| 5,643,283 | A | | 7/1997 | Younker |
| 5,713,853 | A | | 2/1998 | Clark et al. |
| 5,720,754 | A | | 2/1998 | Middleman et al. |
| 5,741,271 | A | | 4/1998 | Nakao et al. |
| 5,846,248 | A | | 12/1998 | Chu et al. |
| 5,997,547 | A | | 12/1999 | Nakao et al. |
| 6,077,274 | A | | 6/2000 | Ouchi et al. |

(Continued)

OTHER PUBLICATIONS

International Search Report, PCT/US2012/045671, Oct. 1, 2012, 12 pages.

(Continued)

*Primary Examiner* — Thomas McEvoy
*Assistant Examiner* — Julie A Szpira
(74) *Attorney, Agent, or Firm* — Cochran Freund & Young LLC; James R. Young

(57) ABSTRACT

Surgical retrieval devices for capturing tissues and fluids in endoscopic and laproscopic operations include a semi-rigid, resiliently collapsible and expandable basket comprising a structural combination of resilient, semi-rigid snare wire and frame wire members that are formed with a yieldable bend configuration that together flare into a basket form when extended out of a catheter. The basket is enhanced by surrounds of net, mesh, or impervious material for retaining smaller bits of tissue or fluids, or with a web of interspersed flexible threads for enhanced tissue retaining capability.

20 Claims, 20 Drawing Sheets

(56) References Cited

U.S. PATENT DOCUMENTS

| | | |
|---|---|---|
| 6,183,482 B1 | 2/2001 | Bates et al. |
| 6,217,589 B1 | 4/2001 | McAlister |
| 6,224,612 B1 | 5/2001 | Bates et al. |
| 6,235,026 B1 | 5/2001 | Smith |
| 6,267,776 B1 | 7/2001 | O'Connell |
| 6,348,056 B1 | 2/2002 | Bates et al. |
| 6,458,145 B1 | 10/2002 | Ravinscroft et al. |
| 6,500,182 B2 | 12/2002 | Foster |
| 6,585,734 B2 | 7/2003 | Levinson |
| 6,656,191 B2 | 12/2003 | Ouchi |
| 6,673,080 B2 | 1/2004 | Reynolds et al. |
| 6,743,237 B2 * | 6/2004 | Dhindsa ............ 606/127 |
| 6,814,739 B2 | 11/2004 | Secrest et al. |
| 6,833,000 B2 | 12/2004 | Levinson |
| 7,270,663 B2 | 9/2007 | Nakao |
| 7,326,220 B1 | 2/2008 | Goldstein |
| 7,678,119 B2 | 3/2010 | Little et al. |
| 7,914,540 B2 * | 3/2011 | Schwartz et al. ...... 606/128 |
| 2002/0042617 A1 | 4/2002 | Ouchi |
| 2003/0109889 A1 | 6/2003 | Mercereau |
| 2003/0176888 A1 | 9/2003 | O'Connell |
| 2004/0059345 A1 | 3/2004 | Nakao |
| 2004/0199048 A1 * | 10/2004 | Clayman et al. ......... 600/104 |
| 2005/0119668 A1 | 6/2005 | Teague |
| 2005/0267489 A1 | 12/2005 | Secrest |
| 2006/0100641 A1 | 5/2006 | Teague |
| 2006/0129166 A1 | 6/2006 | Lavelle |
| 2007/0016224 A1 * | 1/2007 | Nakao ................ 606/113 |
| 2007/0016225 A1 * | 1/2007 | Nakao ................ 606/114 |
| 2007/0255289 A1 | 11/2007 | Nakao |
| 2008/0091215 A1 * | 4/2008 | Saleh ................ 606/113 |
| 2008/0306336 A1 * | 12/2008 | Kaye et al. ............ 600/106 |

OTHER PUBLICATIONS

Supplementary Partial European Search Report, EP 12 81 8329, Feb. 12, 2015, 6 pages.

* cited by examiner

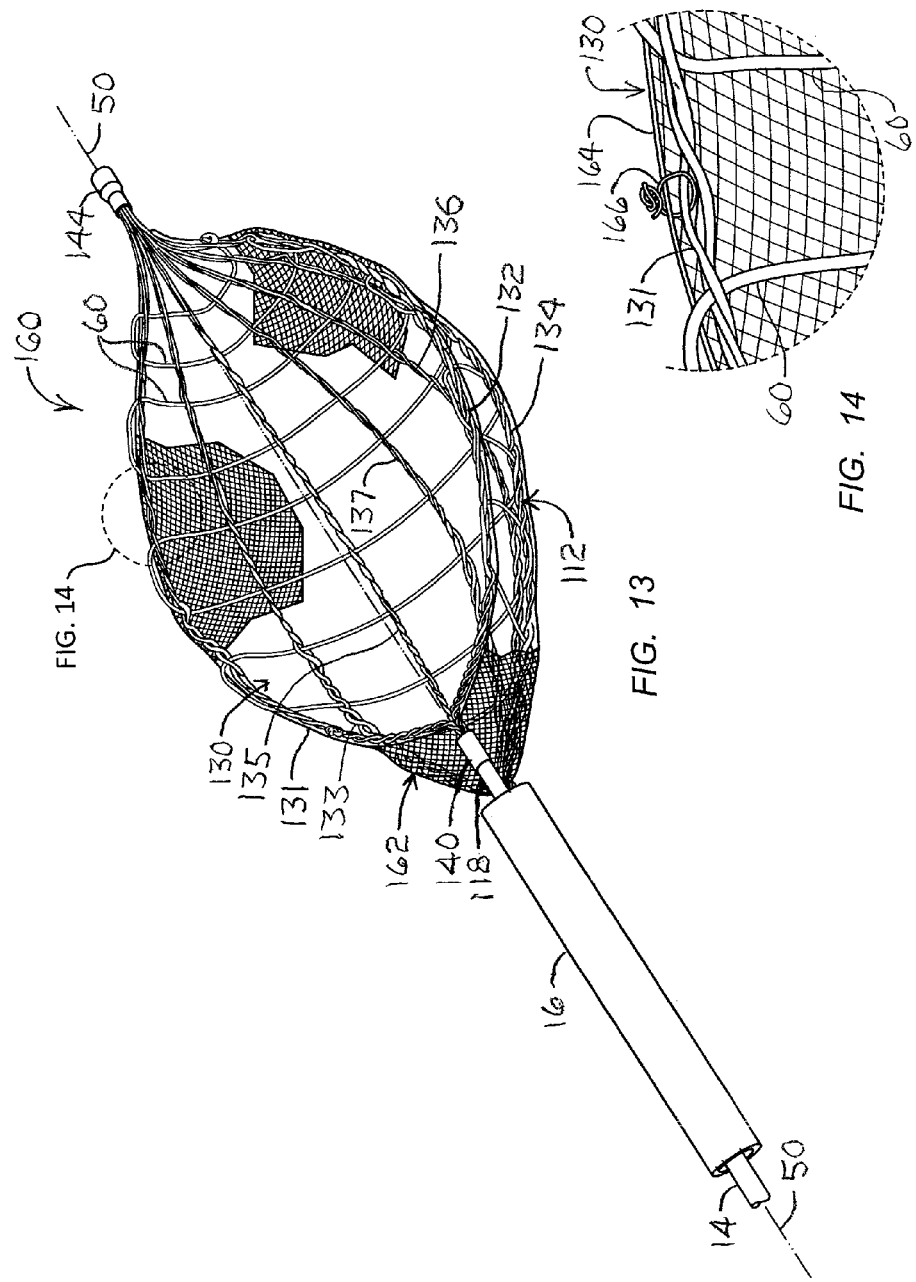

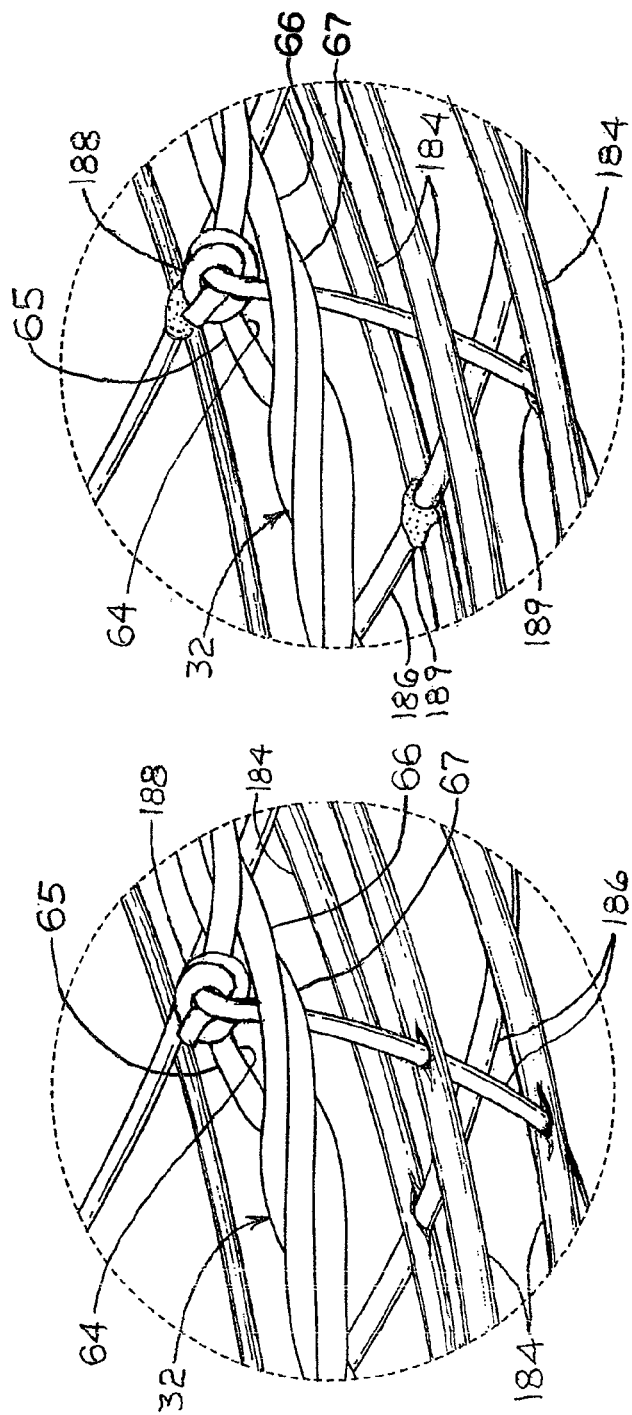

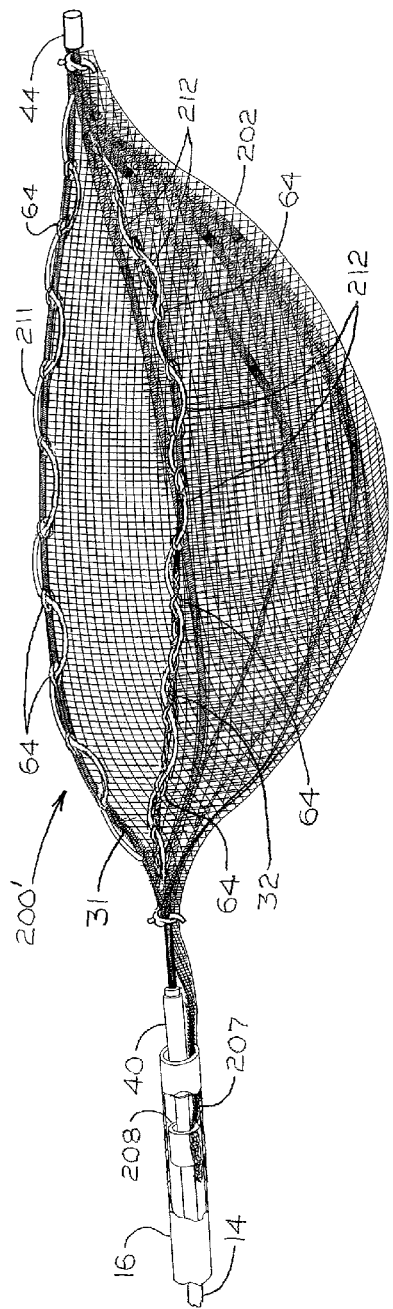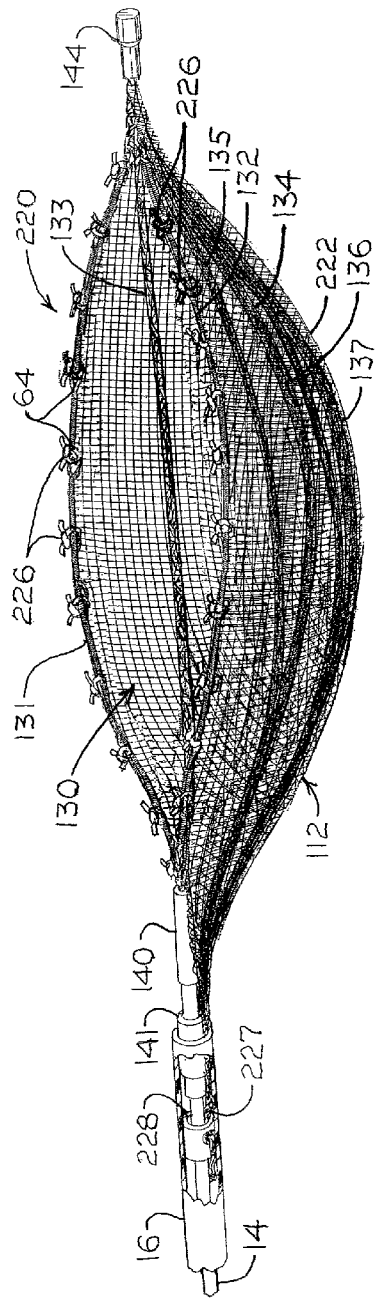

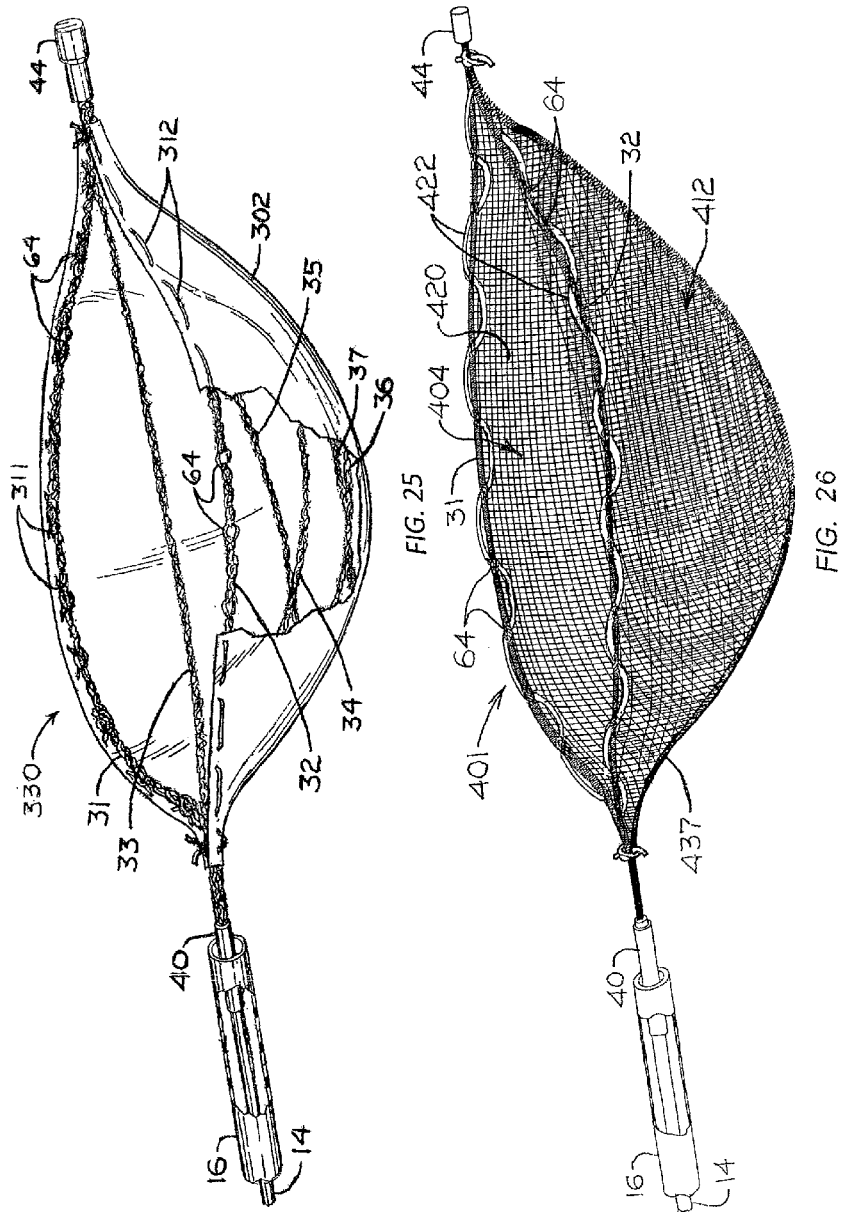

US 9,101,342 B2

SURGICAL RETRIEVAL APPARATUS AND METHOD WITH SEMI-RIGIDLY EXTENDABLE AND COLLAPSIBLE BASKET

TECHNICAL FIELD

The present invention is related to endoscopic surgical devices for capturing and removing tissue pieces and other materials from insides of organs or body cavities accessed endoscopically.

BACKGROUND

Endoscopic surgery procedures are common in many medical research and practice fields for myriad purposes, for example, to access, diagnose, and treat or excise abnormalities or conditions in interior portions of a patient's body or internal organs that would not be visible or accessible to a surgeon's vision or hands without more extensive or invasive incisions or surgical procedures. An endoscope generally, but not always, comprises some type of rigid or flexible tube, sometimes called a catheter, a light delivery system to illuminate the target object or tissue, a lens system for transmitting images of the target object or tissue through the tube to the viewer, an eyepiece and/or camera, and often one or more additional lumens to accommodate entry of some kind of medical or surgical instrument or manipulator. Some endoscopic instruments include only the surgical instruments disposed in and deployed by an elongated tube (e.g., catheter), but not the optical components, in which case they may be used concurrently with another endoscope that does include optical components. Endoscope and endoscopy as used herein are broader terms that encompass various types of such instruments and procedures, including, but not limited to, laparoscopy, bronchoscopy, colonoscopy, and arthroscopy. Endoscopic procedures are common in myriad types of medical specialties and body organs or cavities, including, for example, the gastrointestinal tract, the respiratory tract, the urinary tract, the ear, the reproductive system, normally closed body cavities via small incisions such as the pelvic cavity, joints, organs of the chest, and others. In some of such procedures, various sized and kinds of pieces of tissues are cut or otherwise separated from the organ or target object of the surgery, and, in others, various kinds of other materials are captured and removed from the organs or target objects in the body. In some procedures, such separated pieces of tissue or other materials can be removed by irrigation and suctioning, but others are removed with instruments that are designed to capture and hold them mechanically as they are removed from the organ or body through or with the endoscopic instrument.

An example of an instrument designed to capture and hold separated pieces of tissue or other materials mechanically in endoscopic procedures for removal from organs or bodies is shown in U.S. patent application Ser. No. 11/635,700, filed by Rafic Saleh, on Dec. 6, 2006 (Publication No. 2008/0091215 A1), which is incorporated by reference herein for all that it teaches and discloses. Other examples of such instruments are shown in U.S. Pat. No. 6,656,191, issued on Dec. 2, 2003, to T. Ouchi; U.S. Pat. No. 5,643,283, issued on Jul. 1, 1997, to M Younker; U.S. Pat. No. 5,201,740, issued on Apr. 13, 1993, to N. Nakao; U.S. Pat. No. 5,201,740, issued on Mar. 2, 1993, to N. Nakao; U.S. Pat. No. 6,814,739, issued on Nov. 9, 2004, to D Secrest and M. Younker; and U.S. patent application Ser. No. 11/182,543, filed by N. Nakao on Jul. 15, 2005 (Publication No. 2007/0016224 A1).

The foregoing examples of related art and limitations related therewith are intended to be illustrative and not exclusive, and they do not imply any limitations on the inventions described and claimed herein. Various limitations of the related art will become apparent to those skilled in the art upon reading and understanding of the specification below and of the accompanying drawings.

BRIEF DESCRIPTION OF THE DRAWINGS

The accompanying drawings, which are incorporated herein and form a part of the specification, illustrate some, but not the only or exclusive, example embodiments and/or features. It is intended that the embodiments and figures disclosed herein are to be considered illustrative rather than limiting.

In the drawings:

FIG. 13 is a perspective view from above of another example embodiment endoscopic surgical retrieval device that includes a net surround extending from the snare components at the mouth of the basket around the longitudinal frame members for further closing the open spaces between the longitudinal frame members for catching and retrieving smaller particles;

FIG. 14 is an enlarged view of a portion of the endoscopic retrieval device of FIG. 13 illustrating one example attachment of the net to the snare components;

FIG. 17 an enlarged view of a portion of the endoscopic retrieval device of FIG. 16 illustrating diagrammatically examples connections of the horizontal flexible thread loops to the vertical suspension wires and of the vertical suspension wires to the snare components;

FIG. 18 is an enlarged view similar to FIG. 17 showing another example connection of the horizontal flexible thread loops to the vertical suspension wires;

FIG. 21 is a perspective view similar to FIG. 19, but with the net surround attached by laces to the rim or snare wires;

FIG. 22 is a perspective view of an example retrieval device similar to the example retrieval device in FIGS. 8-12 equipped with a net surround;

FIG. 25 is a perspective view of another example retrieval device with an impermeable surround material backing for the basket;

FIG. 26 is a perspective view of another example retrieval device showing one wire frame member in addition to the snare wires that form the basket.

DETAILED DESCRIPTION OF EXAMPLE IMPLEMENTATIONS AND EMBODIMENTS

Figure 1:
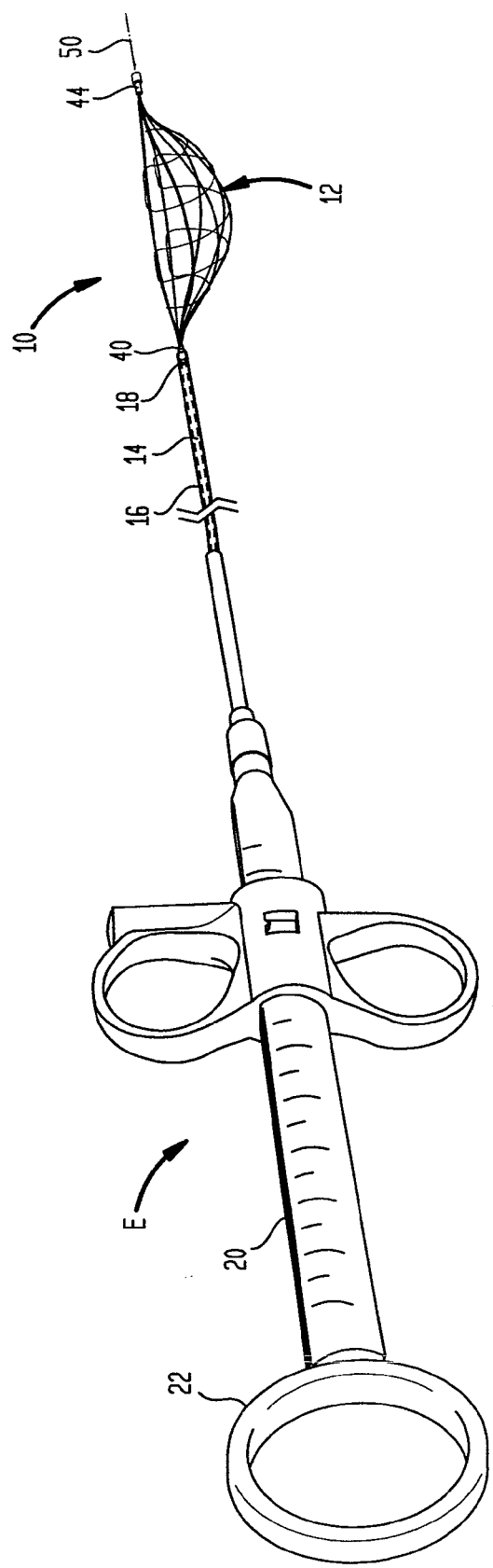
FIG. 1 is a perspective view of an example endoscopic instrument equipped with an example implementation of the surgical retrieval device of this invention.
Figure 2:
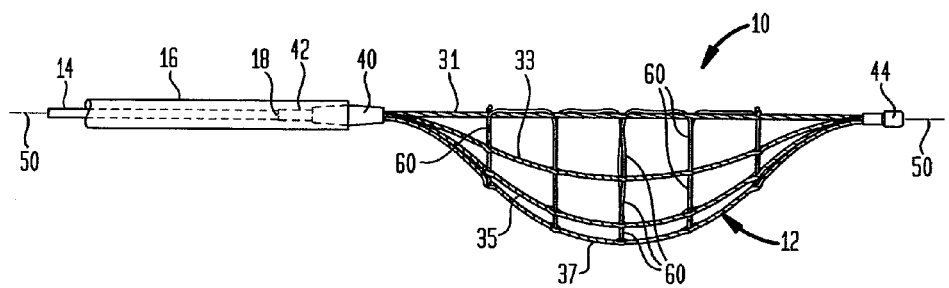
FIG. 2 is side elevation view of the example endoscopic surgical retrieval device of FIG. 1.
Figure 3:
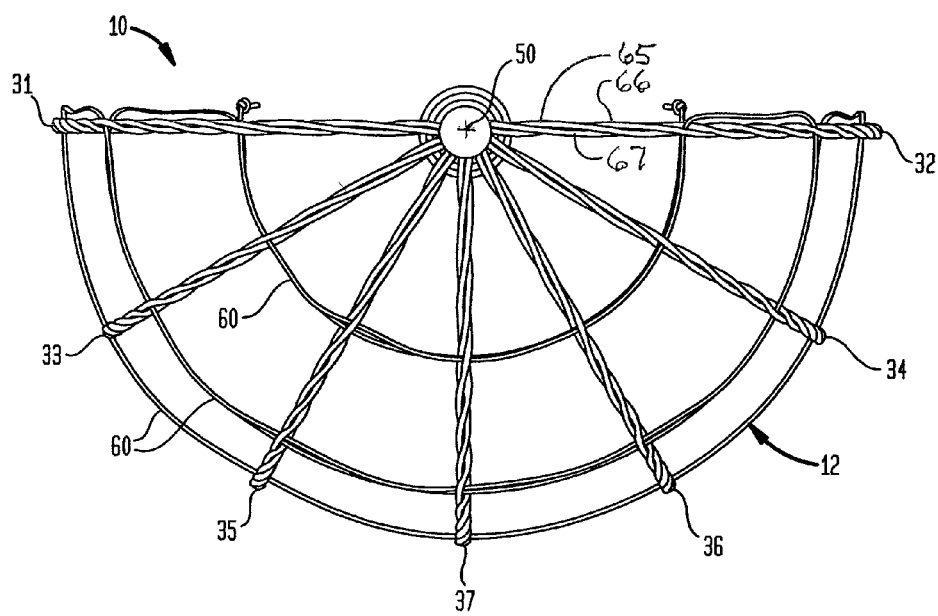
FIG. 3 is a front elevation view of the example endoscopic surgical retrieval device of FIG. 1.

An example endoscopic instrument E equipped with an example implementation of the surgical retrieval device 10 of this invention 10 shown in FIGS. 1-7 can be used for capturing and removing or retrieving tissue pieces and other materials from inside body organs or cavities during endoscopic procedures, including, for example, but not for limitation, gastroenterological, pulmonary, laparoscopic, urological, fluoroscopic, and others. This example endoscopic surgical retrieval device 10 includes a semi-rigid basket 12 comprising an advantageous structural combination of resilient, semi-rigid wire frame members 31, 32, 33, 34, 35, 36, and 37 and flexible thread segments 60 that enhances tissue and material capturing capability, durability, and reliability over prior art baskets with wires and/or net-type nets and bags. The resilient, semi-rigid wires in U.S. patent application Ser. No. 11/635,700 provide certain advantages, including durability that withstands the pressures and forces exerted on it during rotations and other manipulations of the device during use in attempting to capture tissue pieces or other materials in endoscopic surgical procedures, which can be significant on such small and somewhat delicate devices. However, they are not reliable for holding captured tissue pieces and other materials that can slip too easily through the spaces between the angularly spaced wires. On the other hand, the soft, sagging, and droopy nets and bags of other prior art devices are too delicate and not very durable and reliable. They often fold, close, and even detach from their mountings due to the pressures and forces resulting from ordinary manipulations of the instruments in body cavities and organs, thus rendering them virtually useless.

The structural combination of the wire frame members 31, 32, 33, 34, 35, 36, and 37 with the flexible thread segments 60 in the example basket 12 in FIGS. 1-7 not only provide the durability of the wire frame members 31, 32, 33, 34, 35, 36, and 37, which take the brunt of the pressures and forces applied during manipulations, enhanced by the retaining capability of the flexible thread segments 60, but also the structure enhances the durability and reliability of the flexible thread segments 60 themselves as part of the structure. As will be described in more detail below, the thread segments 60 are laced through and/or attached to a plurality of locations or points along the lengths of the wire frame members 31, 32, 33, 34, 35, 36, and 37, so that, even if one or several thread segments 60 or parts of the thread segments 60 should be broken or detached during use, the remaining thread segments 60 by and large stay in place, which enhances both durability of the device and reliability in retaining the tissue pieces and other materials captured in the basket 12.

The basket 12 of the retrieval device 10 is mounted on the distal end 18 of a cable 14 (e.g., stiff wire or tube capable of pushing and pulling), which extends through a lumen in a catheter 16, which may or may not have other lumens (not shown) for optical components, irrigation fluids, or other surgical devices or tools (not shown) that may be used along with the surgical retrieval device 10. Alternatively, the catheter 16 itself, along with the cable 14 and basket 12, can be deployed through a lumen or working channel in another, larger catheter (not shown) that might include lighting and optical components or additional instruments, irrigation lumens, and the like, as would be familiar to persons skilled in the art once they understand this invention. The catheter 16 can be attached to a conventional endoscopic handle 20 for easy manipulation, and the cable 14 can be attached to a telescopic plunger device 22 that extends slideably into the handle 22, where it attaches (not shown) to the cable 14. The plunger device 14 can then be moved longitudinally forwardly and backwardly to extend and retract the distal end 18 of the cable 14 and the semi-rigid basket 12 from and into the catheter 16, as will also be understood by persons skilled in the art once they understand this invention. In this description, the directional prepositions of up, upwardly, down, downwardly, front, back, top, upper, bottom, lower, left, right, and other such terms refer to the device as it is oriented and appears in the drawings and are used for convenience only; they are not intended to be limiting or to imply that the device has to be used or positioned in any particular orientation.

Figure 4:
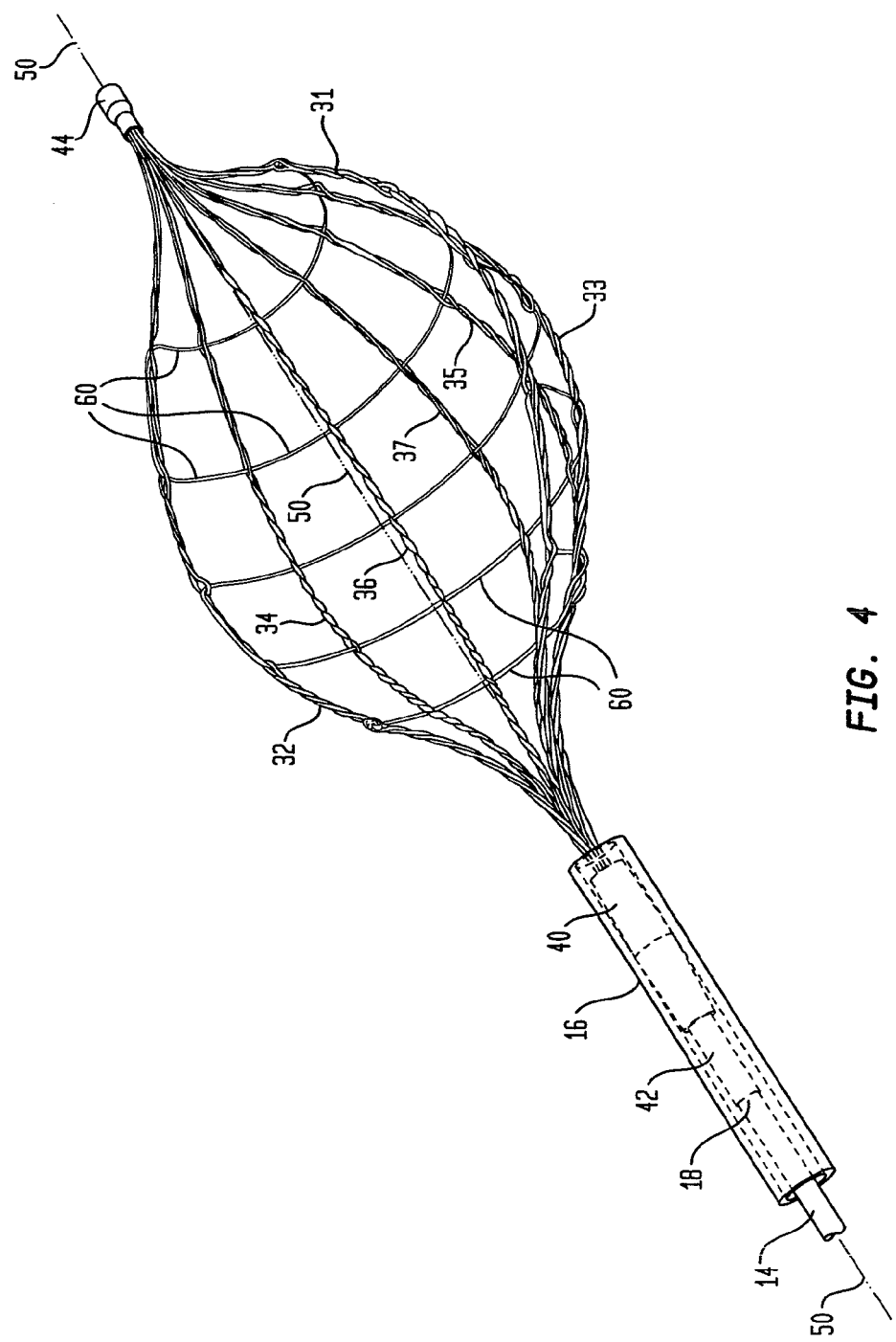
FIG. 4 is an enlarged perspective view of the example endoscopic surgical retrieval device of FIG. 1 looking at the top or open mouth portion of the semi-rigid basket component.
Figure 5:
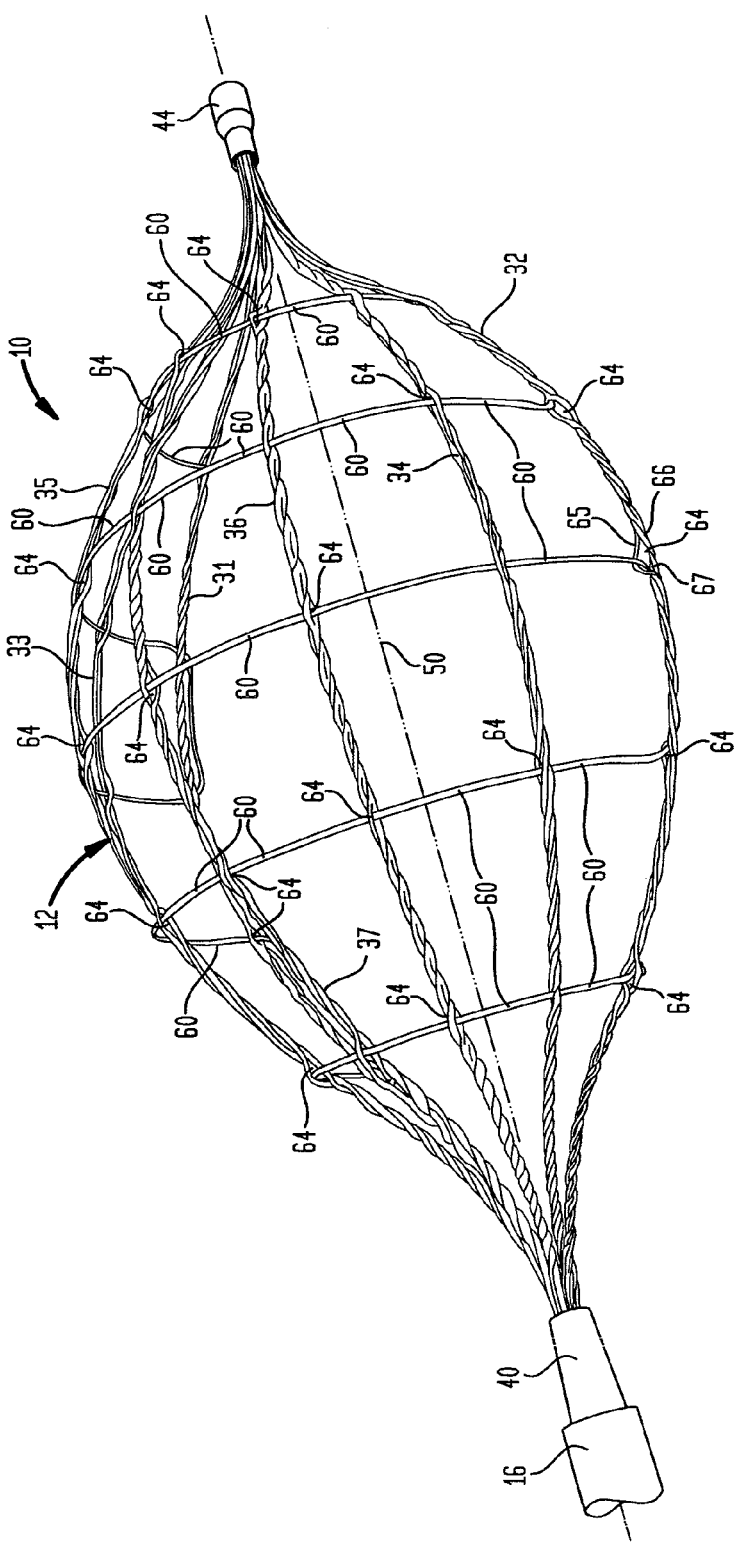
FIG. 5 is a further enlarged perspective view of the example endoscopic surgical retrieval device of FIG. 1 looking at the bottom enclosure portion of the semi-rigid basket component.
Figure 6:
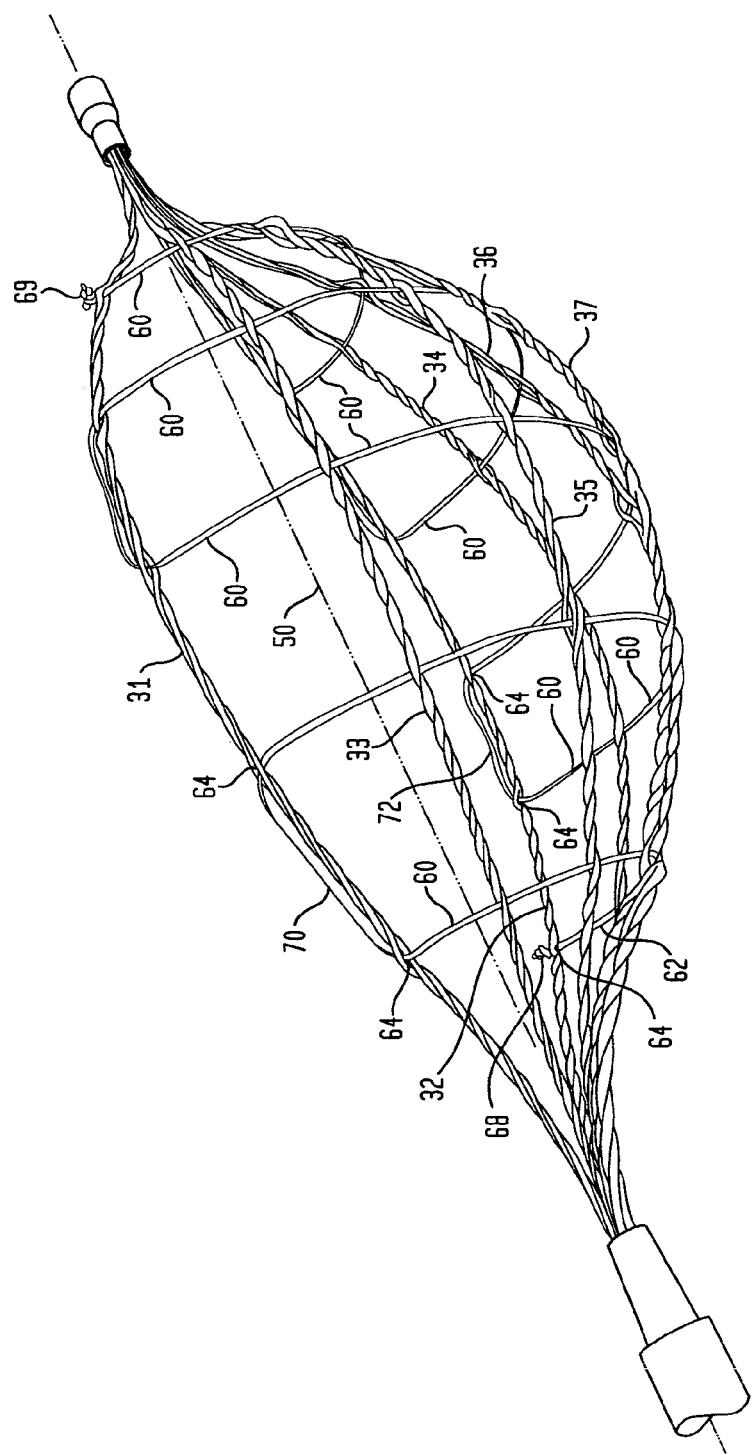
FIG. 6 is an enlarged perspective view of the example endoscopic surgical retrieval device of FIG. 1 slightly rotated to look at a side of the semi-rigid basket component.
Figure 7:
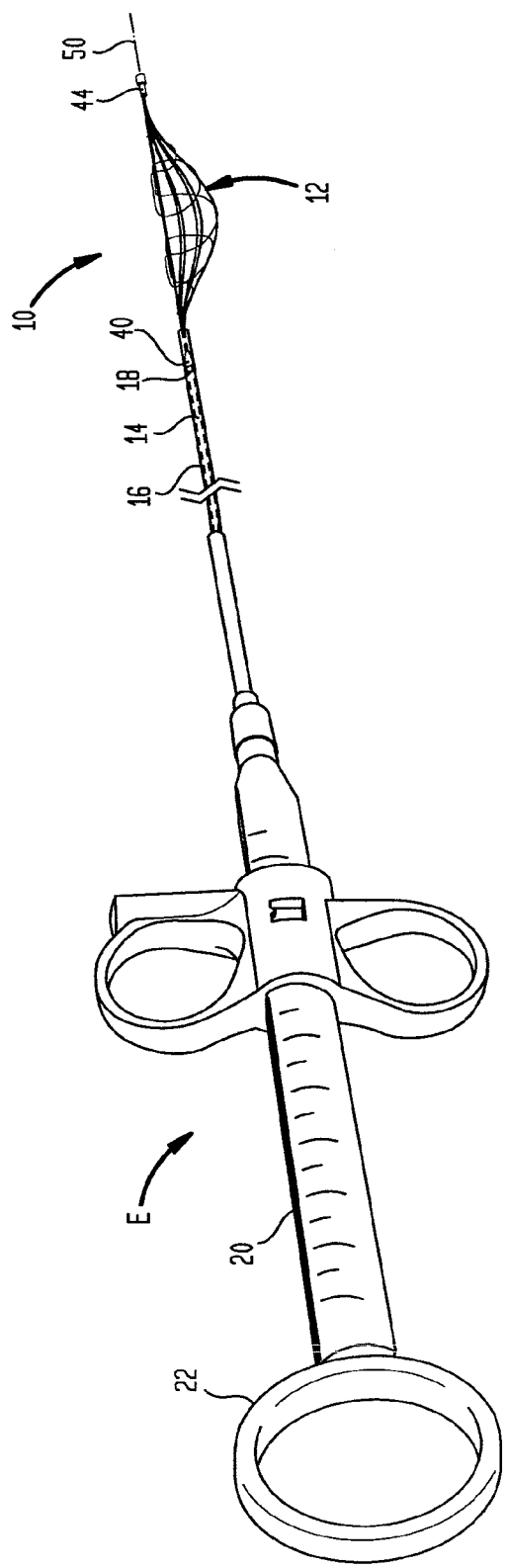
FIG. 7 is a perspective view of the example instrument similar to FIG. 1, but showing the semi-rigid basket component partially retracted into the catheter.

With reference now primarily to FIGS. 2-6 with secondary reference to FIGS. 1 and 7, the semi-rigid basket 12 comprises a plurality of generally longitudinally extending, semi-rigid, resiliently deformable wires, for example, the wires 31, 32, 33, 34, 35, 36, and 37, the proximal ends of which are gathered and fastened together in immovable relation to each other by a ferrule 40 and connected by a coupling 42 to the distal end 18 of the cable 14. The proximal ends of the wires 31, 32, 33, 34, 35, 36, and 37 are gathered and fastened together in immovable relation to each other by another ferrule 44. The wires 31, 32, 33, 34, 35, 36, and 37 are preformed or bent into bowed shapes, as best seen in FIGS. 4-6, so that, when they are fastened together in the relative orientations to each other by the proximal ferrule 40 and the distal ferrule 44 as shown in FIGS. 2-6, they flare radially outward from the longitudinal axis 50 in angularly spaced relation to each other about the longitudinal axis 50. The top two wires, i.e., rim or snare wires 31, 32, are shown to be coplanar, thus flaring 180 degrees diametrically opposite each other, in the example device 10 in FIGS. 1-7 to create a wide open mouth for the basket 12 for ease of capturing tissue pieces and other materials (not shown) during endoscopic surgical procedures, while the other wires 33, 34, 35, 36, and 37 are positioned to flare radially outward at more closely spaced angles to each other to form the rest of the structural frame of the basket 12. Therefore, the two tip wires 31, 32 are sometimes called the snare components in this description because of their primary function of making the initial catch or capture of the tissue pieces or other particles, while the remaining wires 33, 34, 35, 36, 37 are sometimes called the longitudinal basket frame members. For example, with the seven wires 31, 32, 33, 34, 35, 36, and 37 of the example device 10 in FIGS. 1-7, the angular spacing between the snare wires 31, 32 and the adjacent wires 33, 34, 35, 36, 37 that form the basket frame can be equal at 30 degrees. Of course, other angular spacings between adjacent wires 31, 32, 33, 34, 35, 36, and 37, including something different than the 180 degrees wide open mouth, can also be used for particular purposes or preferences.

The semi-rigid basket 12 in the example device 10 is completed with flexible thread segments 60 extending transversely between adjacent ones of the wires 31, 32, 33, 34, 35, 36, and 37 at longitudinally spaced distances from each other to effectively make the open spaces between the wire frame members 31, 32, 33, 34, 35, 36, and 37 smaller, thus able to capture and retain smaller tissue pieces and other material, which creates a more effective basket than just the wire frame members 31, 32, 33, 34, 35, 36, and 37 by themselves. While not essential, there are advantages to having the flexible thread segments sized in length to become at least marginally taut when the wire frame members 31, 32, 33, 34, 35, 36, and 37 are fully deployed in their flared relation to each other. Marginally taut for this purpose does not necessarily mean the thread segments 60 are tensioned, but that they are at least not loose enough to be able to overlap adjacent thread segments 60. For example, because of the fastening of the proximal ends of the wire frame members 31, 32, 33, 34, 35, 36, and 37 in immovable relation to each other by the ferrule 40 and fastened by the coupling 42 in immovable relation to the cable 14, rotation of the cable 14 in or along with the catheter 16 by the operator of the device 10 causes the basket 12 to rotate as well. Such rotation of the basket 12 is useful in scooping and other maneuvers to capture tissue pieces and other materials during endoscopic surgery procedures, and the semi-rigid relation of the wire frame members 31, 32, 33, 34, 35, 36, and 37 to each other described above maintains the flared and extended shape of the basket 12 described above and shown in FIGS. 1-6 without folding, drooping, or collapsing during such scooping or other capturing maneuvers, which could be a hindrance to such procedures. By providing the flexible thread segments 60 in lengths that become at least marginally taut when the basket 12 is fully deployed with the wire frame members 31, 32, 33, 34, 35, 36, and 37 fully flared outwardly as described above, the flexible thread segments 60 also retain the shape of the basket 12 without folding, drooping, or collapsing during rotations and other capturing maneuvers of the basket 12, thus do not obscure vision or interfere with the maneuvers while also remaining as effective retaining elements for holding captured tissue pieces and other materials during such procedures.

However, when the basket 12 is retracted back into the catheter 16 (see FIG. 7 wherein the basket 12 is shown partially retracted), the resiliently yieldable, semi-rigid wire frame members 31, 32, 33, 34, 35, 36, and 37 are collapsed by the catheter 16, thereby loosening the flexible thread segments 60, for folding together with the wire frame members 31, 32, 33, 34, 35, 36, and 37 into the catheter 16. In such collapsed condition, the flexible thread segments 60 are pulled by the respective wire frame members 31, 32, 33, 34, 35, 36, and 37 to which they are connected into the catheter 16, which causes the flexible thread segments 60 to form into somewhat folded V-shaped segments between respective adjacent wire frame members 31, 32, 33, 34, 35, 36, and 37 as they are pulled and dragged into the catheter 16. In that formation, the flexible thread segments 60 do not bunch or interfere with the retraction of the collapsed basked 12 into the catheter 16, and they do not interfere with the deployment of the basket 12 out of the catheter 16, either. As the basket 12 is deployed by pushing it out of the distal end of the catheter 16, the resilient, collapsed wire frame members 31, 32, 33, 34, 35, 36, and 37 resume their bowed shapes from the shape memory characteristic of the molecular or crystalline material of which the wire frame members 31, 32, 33, 34, 35, 36, and 37 are made. Suitable materials for the resilient, semi-rigid wire frame members 31, 32, 33, 34, 35, 36, and 37 include, but are not necessarily limited to, stainless steel, nitinal, titanium, or any of a number of synthetic materials that have those properties or characteristics.

The flexible thread segments 60 can be attached to the wire frame members 31, 32, 33, 34, 35, 36, and 37 in myriad ways, one example of which is illustrated in FIGS. 1-6. In this example implementation, a single strand of flexible thread 62 is strung through a plurality of holes or eyes 64 in each of the wire frame members 31, 32, 33, 34, 35, 36, and 37, as perhaps best seen in FIGS. 5 and 6. In this example device 10, each wire frame member 31, 32, 33, 34, 35, 36, and 37 comprises a plurality of wire strands, e.g., strands 65, 66, 67, twisted together to provide an optimum semi-rigidity, shape memory, and resilience. The holes or eyes 64 are formed in the twisted wire frame members 31, 32, 33, 34, 35, 36, and 37 by spreading one of the strands 65, 66, 67 slightly away from the others, as best seen in FIGS. 5, 17, and 18. The single strand of flexible thread 62 can be strung or laced through the myriad holes in any manner or orientation to create spaces between thread segments 60 in any shape, but, in this example shown in FIGS. 1-6, the thread 62 is strung through the eyes 64 in a manner that creates rectangular spaces between the thread segments. It can be seen in several views, but perhaps best in FIG. 6, that a first end of the single strand of thread is provided with a knot 68 that anchors and prevents that end from sliding through the adjacent eye 64 in one of the top wire frame members, for example, the wire frame member 32. The thread 62 then extends transversely across the angular spaces between adjacent wire frame members 34, 36, 37, 35, and 33 and through eyes 64 in those wire frame members to the opposite top wire frame member 31, where it extends through an eye 64 and then parallel to that top wire frame member 31 to the next eye 64 on that wire frame member 31, as indicated at 70. From its extension through that next eye 64 in the wire frame member 31, the thread 62 then extends transversely back across the spaces between, and through respective eyes 64 in, the adjacent wire frame members 33, 35, 37, 36, and 34 to another eye 64 in the top wire frame member 31, where it extends through that eye 64 and then parallel to that top wire frame member 32, as indicated at 72. That pattern continues back and forth from one top wire frame member to the other via the intermediate wire frame members to a last eye 64 near the distal end of the basket 12, where the thread terminates in another knot 69 that anchors that terminated end to the wire frame member 31. The opposite ends of the single thread 62 could be anchored to any one or two of the wire frame members 31, 32, 33, 34, 35, 36, and 37. It is advantageous for the length of the thread 62 between the knots 68, 69 to be just the amount that will cause the thread 62 and its segments 60 to become somewhat taut when the basket 12 is fully expanded for the reasons explained above.

The spacing of the holes or eyes 64 in the wire frame members 31, 32, 33, 34, 35, 36, and 37 set the sizes of the rectangular spaces between the thread segments 60. Persons skilled in the art can provide such spacings to be optimally effective for whatever kinds of endoscopic procedures or applications the retrieval device 10 is to be used. In general, it is desirable to provide the spacings at optimal distances to capture and hold the target tissue pieces or other materials while allowing liquids and other smaller materials to flow through spaces between the thread segments 64 and adjacent wire frame members 31, 32, 33, 34, 35, 36, and 37.

Other methods and instrumentalities can also be used for fastening the flexible thread segments 60 onto the wire frame members 31, 32, 33, 34, 35, 36, and 37. For example, the thread can be tied, adhered with surgical glue, or otherwise attached to wire frame members 31, 32, 33, 34, 35, 36, and 37. Also, small inserts (not shown) with holes or eyes can be wound into and between the wire strands 65, 66, 67 of the wire frame members 31, 32, 33, 34, 35, 36, and 37. Also, the wire frame members 31, 32, 33, 34, 35, 36, and 37 can be single strand wires or cords with eyes molded or formed into them. The thread 62 or thread segments 60 can be cotton, nylon, polyester, or any of myriad other flexible thread materials. In some embodiments, the top wire frame members 31, 32 can be heavier or stronger wires, strands, or cords than the other wire frame members 33, 34, 35, 36, 37 in order enhance the ability of those top wire frame members 31, 32 to hold the open shape of the mouth as the basket 12 is rotated and manipulated during endoscopic procedures. For example, but not for limitation, the diameter of the strands 65, 66, 67 of the wire frame members 31, 32, 33, 34, 35, 36, and 37 can be in a range of 0.02 inch to 0.20 inch. In one embodiment the strands 65, 66, 67 for the top wire frame members 31, 32 are 0.15 inch, and the strands 65, 66, 67 for the other wire frame members 33, 34, 35, 36, and 37 are 0.12 inch.

Figure 8:
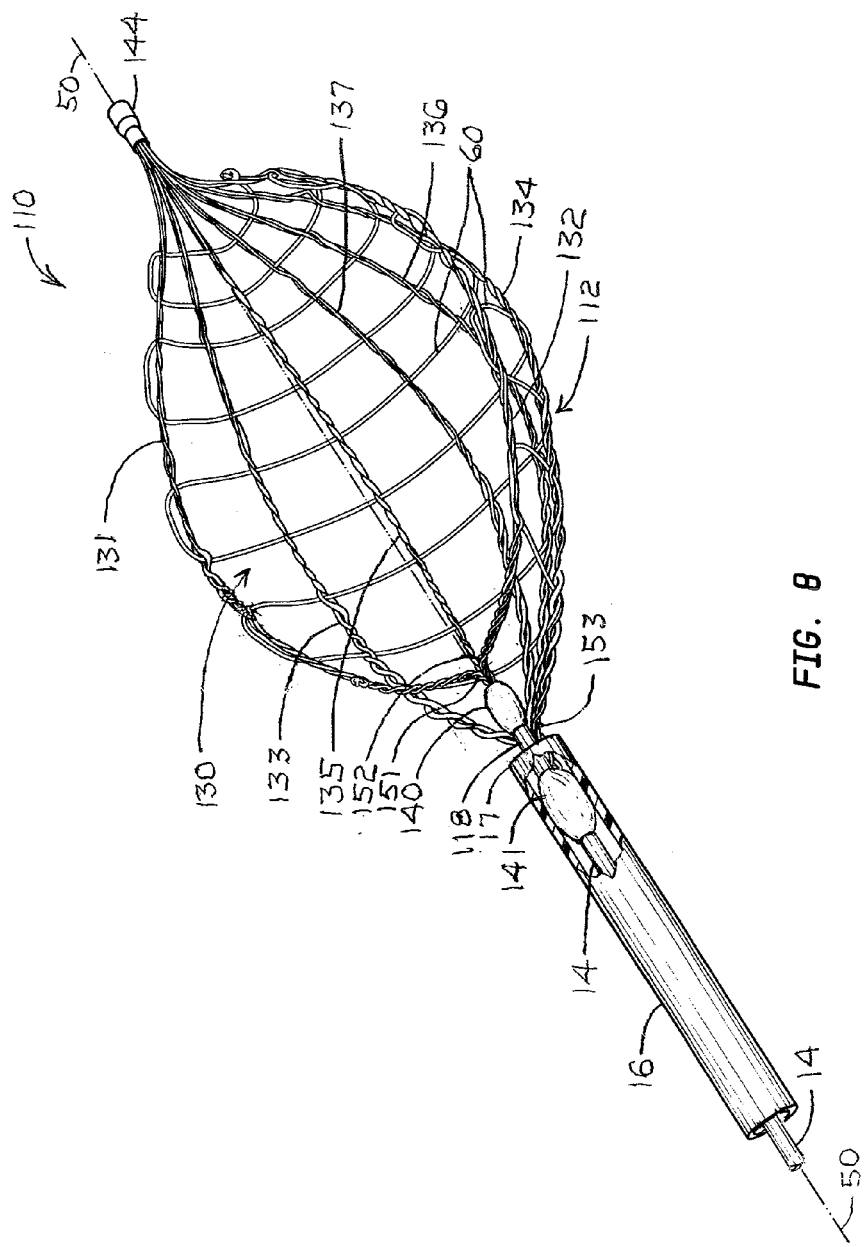
FIG. 8 is a perspective view from above of another example embodiment endoscopic surgical retrieval device that includes a shorter and narrowed snare component at the mouth of the basket, part of the catheter being cut away to reveal the ferrule attachments of the snare and basket components to the cable.
Figure 9:
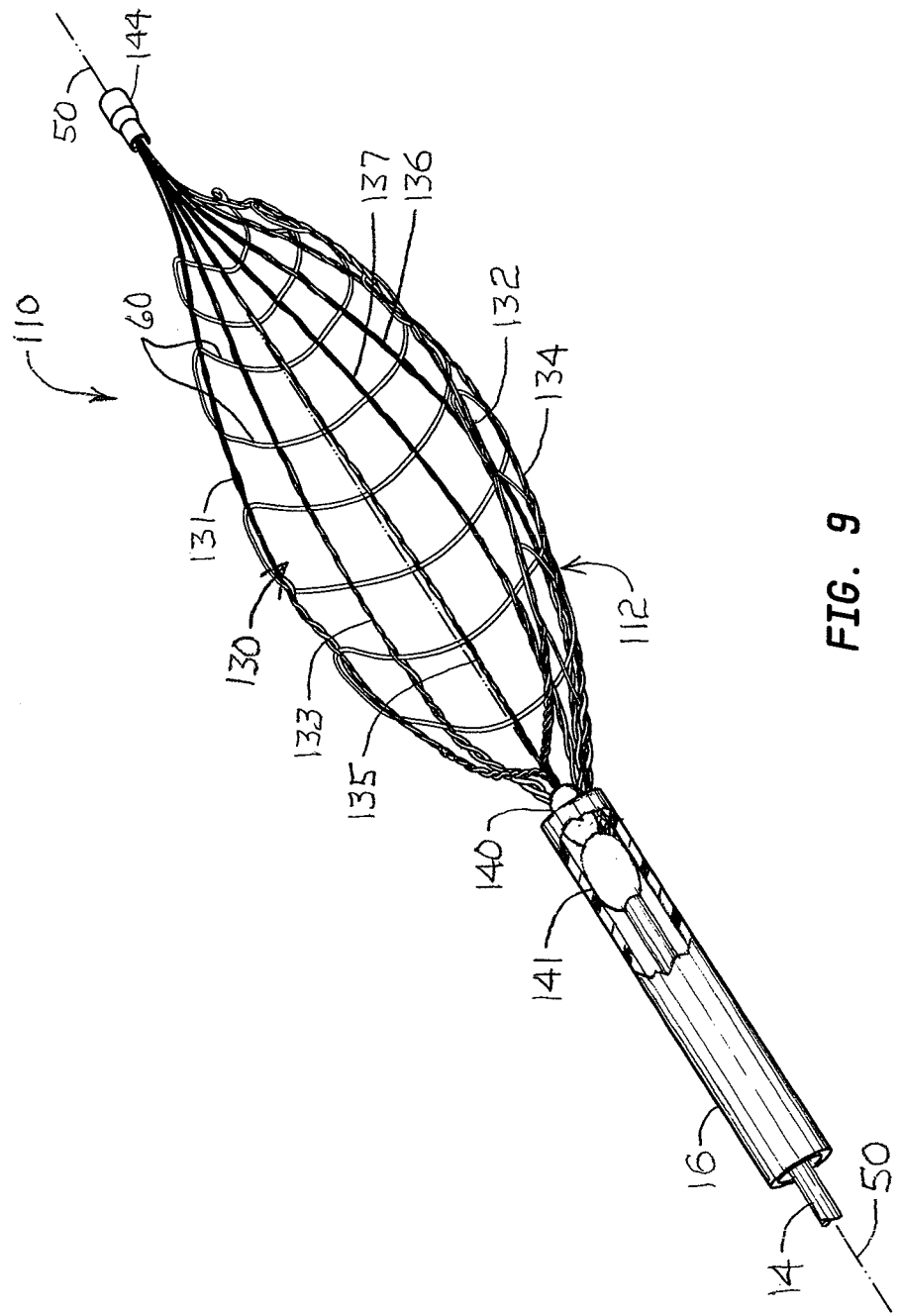
FIG. 9 is a perspective view similar to FIG. 8, but showing the snare and basket partially withdrawn into the catheter.
Figure 10:
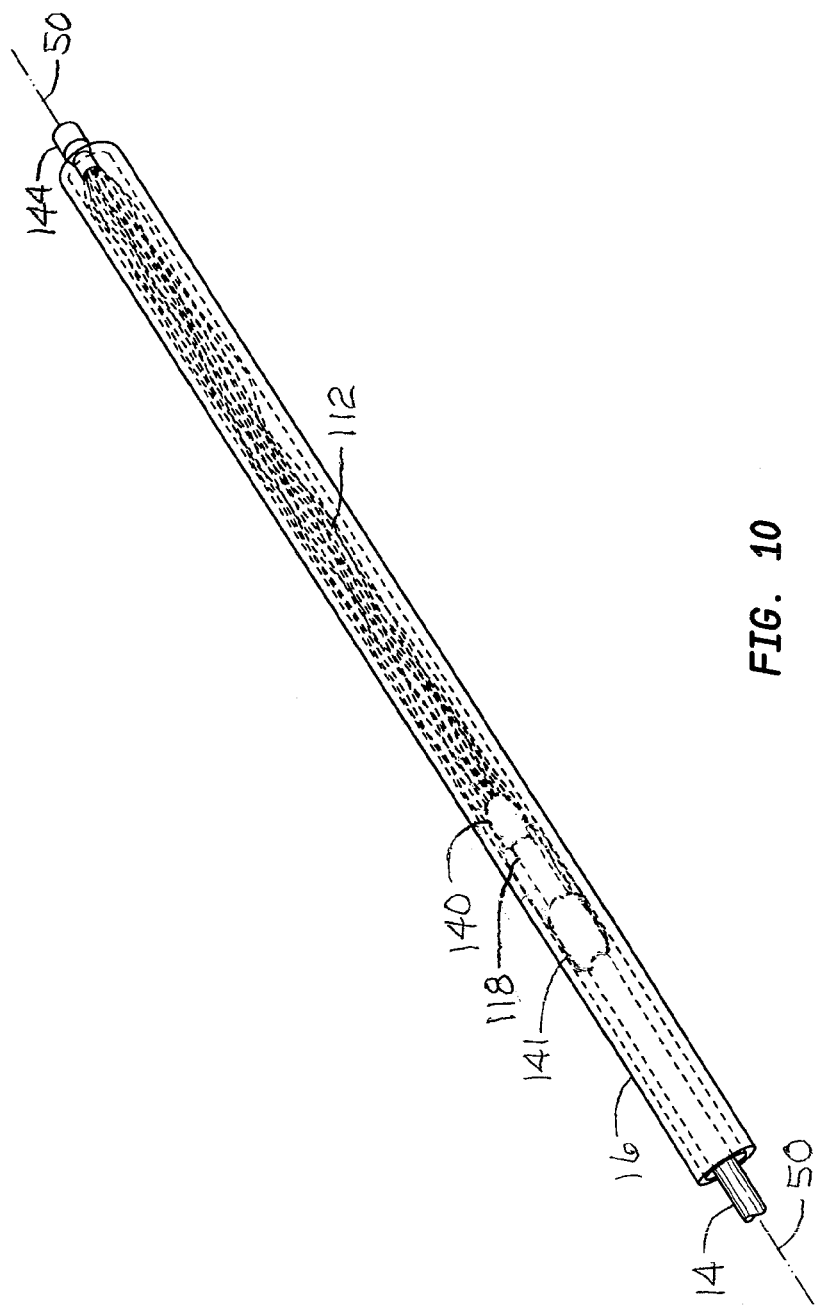
FIG. 10 is a perspective view similar to FIGS. 8 and 9, but showing the snare and basket withdrawn all the way into the catheter.
Figure 11:
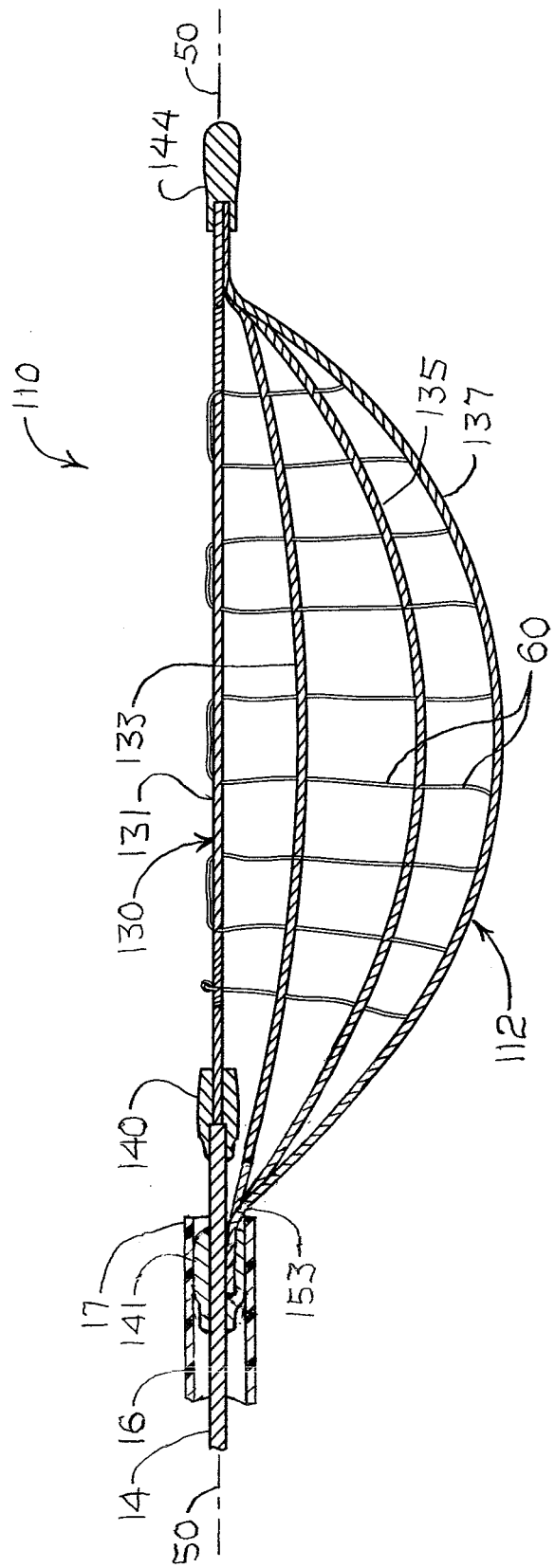
FIG. 11 is a cross-section view in elevation of the example alternate embodiment of FIG. 8 showing the snare and basket components in extended mode.

Another example alternate embodiment retrieval device 110 is shown diagrammatically in FIGS. 8-11 with a narrowed snare and mouth 130 that function semi-independently from the other basket components. As in the previous example embodiment described above, the mouth is formed by a pair of snare wires 131, 132, which are shorter than the other longitudinal basket frame members 133, 134, 135, 136, and 137, which are similar to the longitudinal frame members 33, 34, 35, 36, and 37 described above regarding the example embodiment in FIGS. 1-7. Also, while all of the snare wires 131, 132 and longitudinal frame wires 133, 134, 135, 136, and 137 in the example retrieval device 110 have their distal ends bound in a common distal ferrule 144 similar to the example embodiment shown in FIGS. 1-7, only the proximal ends of the snare wires 131, 132 are bound together in the proximal ferrule 140 attached to the distal end 18 of the cable 14. The proximal ends of the longitudinal wire frame members 133, 134, 135, 136, and 137 are bound together in a slidable ferrule 141 that is mounted in a slidable manner on the cable 14 before the proximal ferrule 140, as best seen in FIGS. 8 and 11.

As best seen in FIG. 8, the snare wires 131, 132 are bent or kinked at 151, 152 just outside the proximal ferrule 140 to provide a yieldable outward flare bias in the snare wires 131, 132 so that they tend to flare outwardly from the longitudinal axis 50 when they emerge and are out of the catheter 16, but also so that the distal end 17 of the catheter 16 causes them to collapse inwardly toward the longitudinal axis 50, thereby closing the mouth 130, as the snare wires 131, 132 are withdrawn by the cable 14 into the catheter 16. Similarly, the longitudinal basket frame wires 133, 134, 135, 136, 137 are bent or kinked just outside the slidable ferrule 141, as indicated generally at 153 for all of the wires 133, 134, 135, 136, 137, so that they tend to flare outwardly from the longitudinal axis 50 when they emerge and are out of the catheter 16, but also so that the distal end 17 of the catheter 16 causes them to collapse inwardly toward the longitudinal axis 50, thereby closing the basket 112, as the longitudinal basket frame wires 133, 134, 135, 136, 137 are withdrawn by the cable 14 into the catheter 16.

As also best seen by reference to FIG. 8, when the basket 112 is pushed out of the catheter 16 by the cable 14, the distal ferrule 144 is, of course, the first component to emerge from the distal end 17 of the catheter 16, followed by the snare wires 131, 132 and the basket frame wires 133, 134, 135, 136, 137. Next to emerge from the catheter 16 is the proximal ferrule 140, which may be urged some distance ahead of the slidable catheter by the outward bias of the snare wires 31, 32 as the proximal portions of those snare wires 31, 32 emerge from the catheter 16. Finally, the proximal portions of the basket frame wires 133, 134, 135, 136, 137 emerge from the catheter 16 and fully extend outwardly in relation to the longitudinal axis 50 to form the basket 112, as illustrated in FIGS. 8 and 11.

Figure 12:
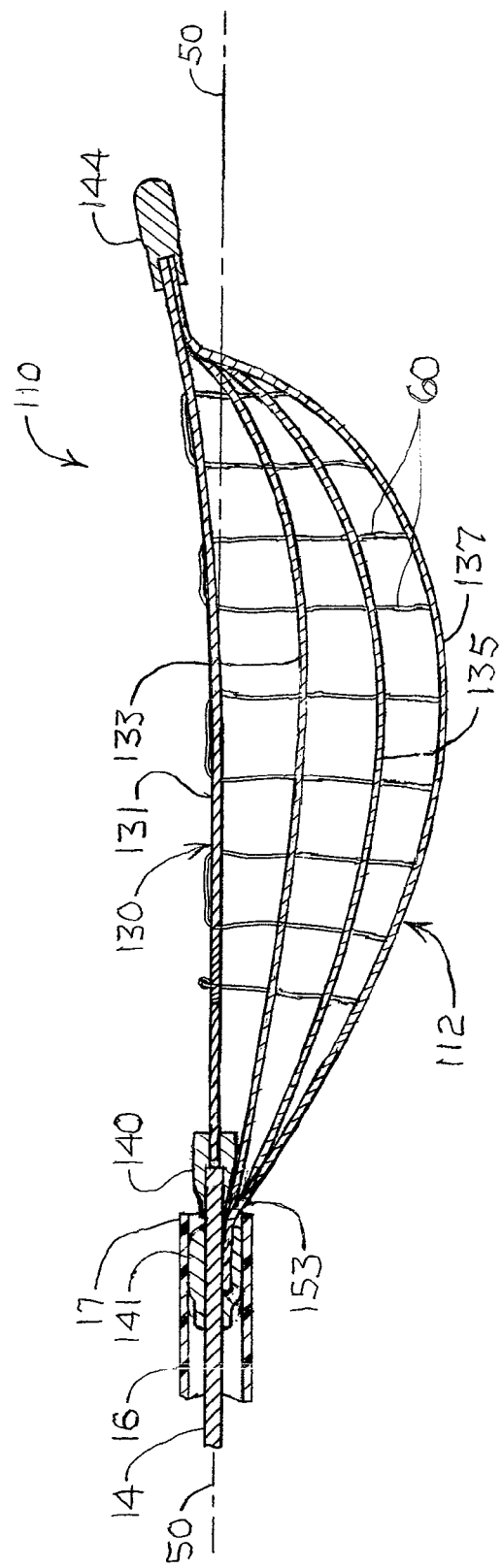
FIG. 12 is a cross-section view similar to FIG. 11, but illustrating the basket as it is initially being withdrawn into the catheter.

In reverse, as the basket 112 is retracted back into the catheter 16 by the cable 14, the bends 153 of the basket wires 133, 134, 135, 136, 137 at the distal end 17 of the catheter 16 initially resist withdrawal of the basket wires 133, 134, 135, 136, 137 into the catheter 16, while the cable 14 sliding through the slidable ferrule 141 pulls the proximal ferrule 140 and snare wires 131, 132 back toward and to the catheter 16, as best seen in FIG. 12. As the proximal ferrule 140 and snare wires 131, 132 are pulled back to the catheter 16 in this manner while the basket wires 133, 134, 135, 136, 137 bear on the distal end 17 of the catheter 16 to resist being pulled into the catheter 16, as explained above, the snare wires 131, 132 begin to deform inwardly toward the longitudinal axis 55, thereby narrowing the mouth 130 even more than its width in the fully extended mode and deforming the distal end of the basket 112 upwardly and away from the longitudinal axis 50, as best seen in FIG. 12. Such narrowing of the mouth 130 and deformation of the basket 112 begins to capture tissue pieces (not shown) or other particles in the basket 112.

Then, as the cable 14 pulls the proximal ferrule 140 farther into the catheter 16, as illustrated, for example, in FIGS. 9 and 12, the proximal ferrule 140 abuts the slidable ferrule 141 and begins to force the slidable ferrule 141 and the basket wires 133, 134, 135, 136, 137 that are attached to the slidable ferrule 141 into the catheter 16. As the basket wires 133, 134, 135, 136, 137 and the snare wires 131, 132 are retracted farther into the catheter 16, the basket 112 also begins to narrow, and the mouth 130 continues to close even more, thereby further capturing and holding tissue pieces (not shown) captured by the device 110 in the basket 112. If the cable 14 pulls the proximal ferrule 140 far enough back into the catheter 16, the basket 112 will be withdrawn entirely into the catheter 16, as illustrated by the phantom lines 112 in FIG. 10. As also shown in FIG. 10, when the basket frame wires 33, 34, 35, 36, 37 are pulled by the slidable ferrule 141 far enough back into the catheter 16 so that the bends 153 (FIGS. 8, 11, and 12) in the basket frame wires 33, 34, 35, 36, 37 are resiliently straightened by the catheter 16 and no longer resist withdrawal of the basket frame wires 33, 34, 35, 36, 37 into the catheter 16, compression forces applied to the basket frame wires 33, 34, 35, 36, 37 by the distal ferrule 144, which is pulled by the snare wires 131, 132 and proximal ferrule 140, push the slidable ferrule 141 farther into catheter 16 in relation to the proximal ferrule 140. This resulting space between the proximal ferrule 140 and the slidable ferrule 141, as shown in FIG. 10, therefore, accommodates the longer basket frame wires 33, 34, 35, 36, 37 inside the catheter 16 alongside the shorter snare wires 131, 132, all of which are bound together by the distal ferrule 144 as explained above.

Of course, in practical use, if there is any significant tissue or other particles (not shown) captured in the basket 112, the basket 112 with such tissue pieces or particles might not be withdrawn all the way into the catheter 16, especially if they are too big together with the basket 112 itself to all fit within the lumen of the catheter 16. However, the closed or nearly closed mouth 130 and collapsed or partially collapsed basket 112 when the basket 112 is partially withdrawn into the catheter 16 as explained above is normally effective to hold such tissue pieces or particles securely in the basket 112 as the catheter 16 itself is withdrawn from a patient's body.

Another example embodiment retrieval device 160 shown diagrammatically in FIG. 13 is further equipped with a surround material 162 backing the basket 112 for catching even smaller tissue pieces or particles (not shown) that might escape between the basket frame wires 133, 134, 135, 136, 137 and thread segments 60. In this FIG. 13 example device 160, the basket 112, snare or rim wires 131, 132, basket wires 133, 134, 135, 136, 137, proximal ferrule 140, distal ferrule 144, and other components can be much the same as those in the example embodiment 110 in FIGS. 8-11 and described above, so the common designator numbers indicate the same or similar components or features and need not be described again for an understanding of this example embodiment 160. Some portions of the surround material are missing in the illustration in FIG. 13 so as to not completely conceal other components, but persons skilled in the art will understand that the surround material 162 extends around the basket 112 formed by the frame wires 133, 134, 135, 136, 137 and thread segments 60.

The surround material 162 shown diagrammatically in FIG. 13 is a net or mesh material, although other materials can also be used for various purposes, for example, an impermeable surround material as illustrated in FIG. 25 and described below. The net surround 162 is illustrated in FIG. 13 as being around the outside of the basket 112 so that, when deployed, the basket wires 133, 134, 135, 136, 137 provide and retain the pocket-like shape and structure of the net surround 162 when the basket is extended in its use mode outside of the catheter 16. The top rim 164 of the net surround 162 is show n in FIG. 14 fastened to the snare or rim wires 131, 132, i.e., around the mouth 130 of the basket 112, for example, by small ties 166 of fine wire, thread, or other fastener means such as glue or other fastener instrumentalities. Only one of the ties 166 is shown in FIG. 14, but persons skilled in the art will understand that there are a plurality of such ties to fasten the top rim of the net surround 162 in multiple places along the lengths of the snare wires 131, 132 to fasten the net surround 162 securely to the snare wires 131, 132. When the basket 112 is withdrawn back into the catheter 16 or partially back into the catheter 16, as described above, the net surround 162 is pulled by the small ties 166 attached to the snare wires 131, 132 along with the basket 112 into, or partially into, the catheter 16 as well.

Of course, persons skilled in the art will recognize that other means of fastening the net surround 162 to the snare wires 131, 132 instead of, or in addition to, the ties 166 shown in FIG. 14. Several examples may include laces 211 as shown in FIG. 21 and described below, glue, and others.

Alternatively, the net surround 162 could be positioned inside the basket 112. If positioned inside the basket 112, it may be beneficial to tie or otherwise fasten the net surround 162 at intermediate locations along the frame wires 133, 134, 135, 136, 137 to conform the net surround 162 to the shape of the basket 112 when deployed. Otherwise, the net surround 112 may tend to drift upwardly and block or partially block the mouth 130 of the basket 112, which might interfere with capturing tissue pieces or other particles into the basket 112. As another alternative, the net surround 162 could be used with the basket 112 without the thread segments 60, if desired.

Figure 15:
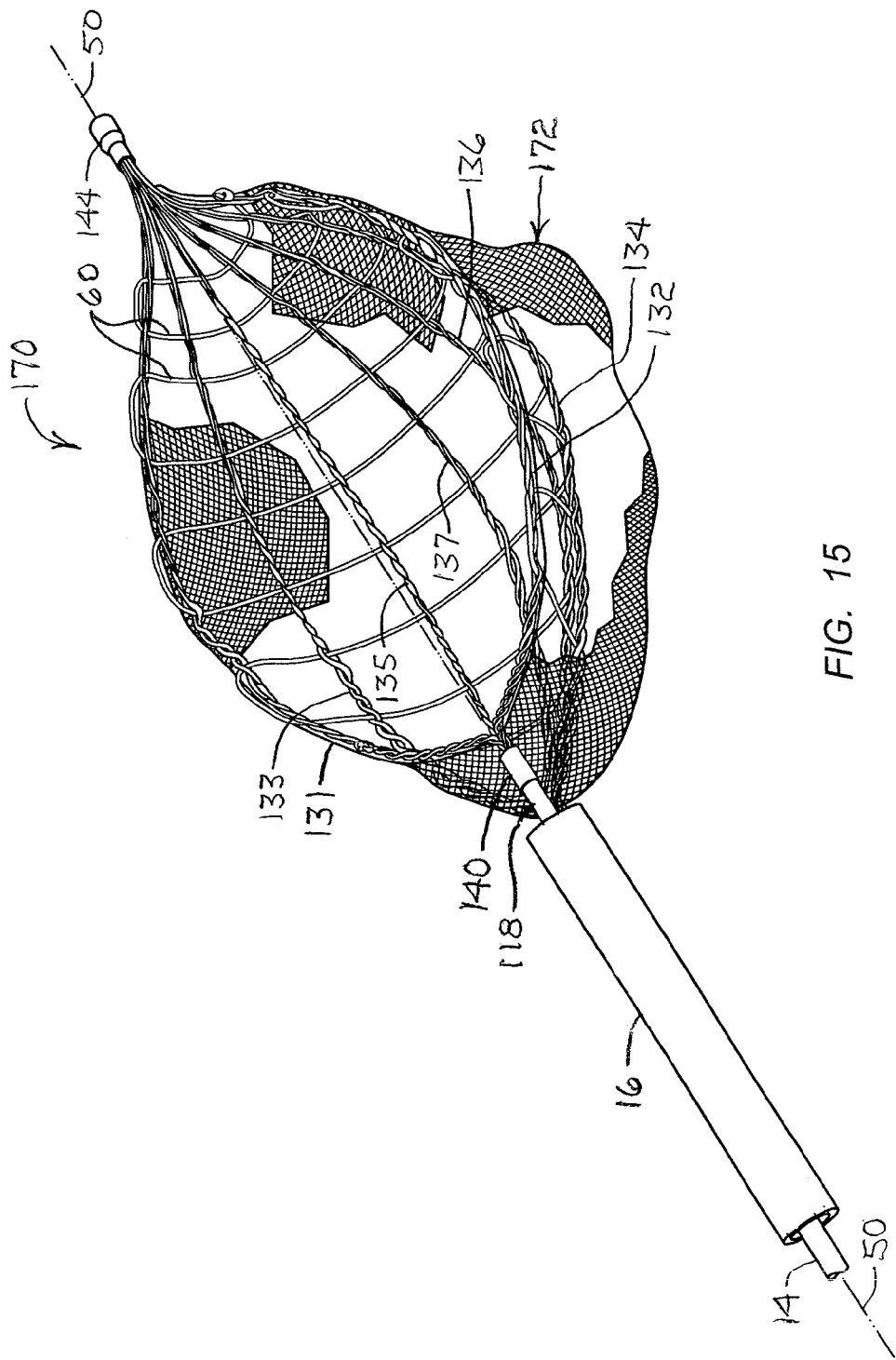
FIG. 15 is a perspective view from above of another example embodiment endoscopic retrieval device similar to FIG. 13, but illustrating a larger net that does not fit snugly against the longitudinal frame members.

Another example embodiment retrieval device 170 shown diagrammatically in FIG. 15 is equipped with a bag 172 for catching small tissue pieces or particles (not shown), similar to the retrieval device embodiment 160 in FIGS. 13 and 14 described above, but the bag 172 in the FIG. 15 embodiment 170 is larger than the net surround 162 in the retrieval device 160 so that it does not have a snug fit with the frame wires as shown in FIG. 13 for the retrieval device 160, but instead extends outwardly beyond the frame wires 133, 134, 135, 136, 137 to form more of a bag than a backing for the basket. Therefore, the bag 172 of the retrieval device 170 may have more holding capacity than the surround material 162 of the retrieval device 160, but the frame wires 133, 134, 135, 136, 137 still retain basket 112 shape, keep the bag 172 open, and prevent the bag 172 from blocking or partially blocking the mouth 130 when the retrieval device 170 is deployed in use mode out of the catheter 16. The illustration in FIG. 15 shows the bag 172 comprising a net or mesh material, e.g., a net bag 172, but the bag 172 could also be made with other material if desired, for example, an impermeable material. The net bag 172 is shown in FIG. 15 with some portions removed so as not to completely conceal other components of the basket 112, but persons skilled in the art will understand that the net bag 172 is a full bag. It can be fastened to the snare wires 131, 132, as described above for the net surround 162 of the retrieval device 160. Also, the net bag 172 can be used with or without the thread segments 60.

Figure 16:
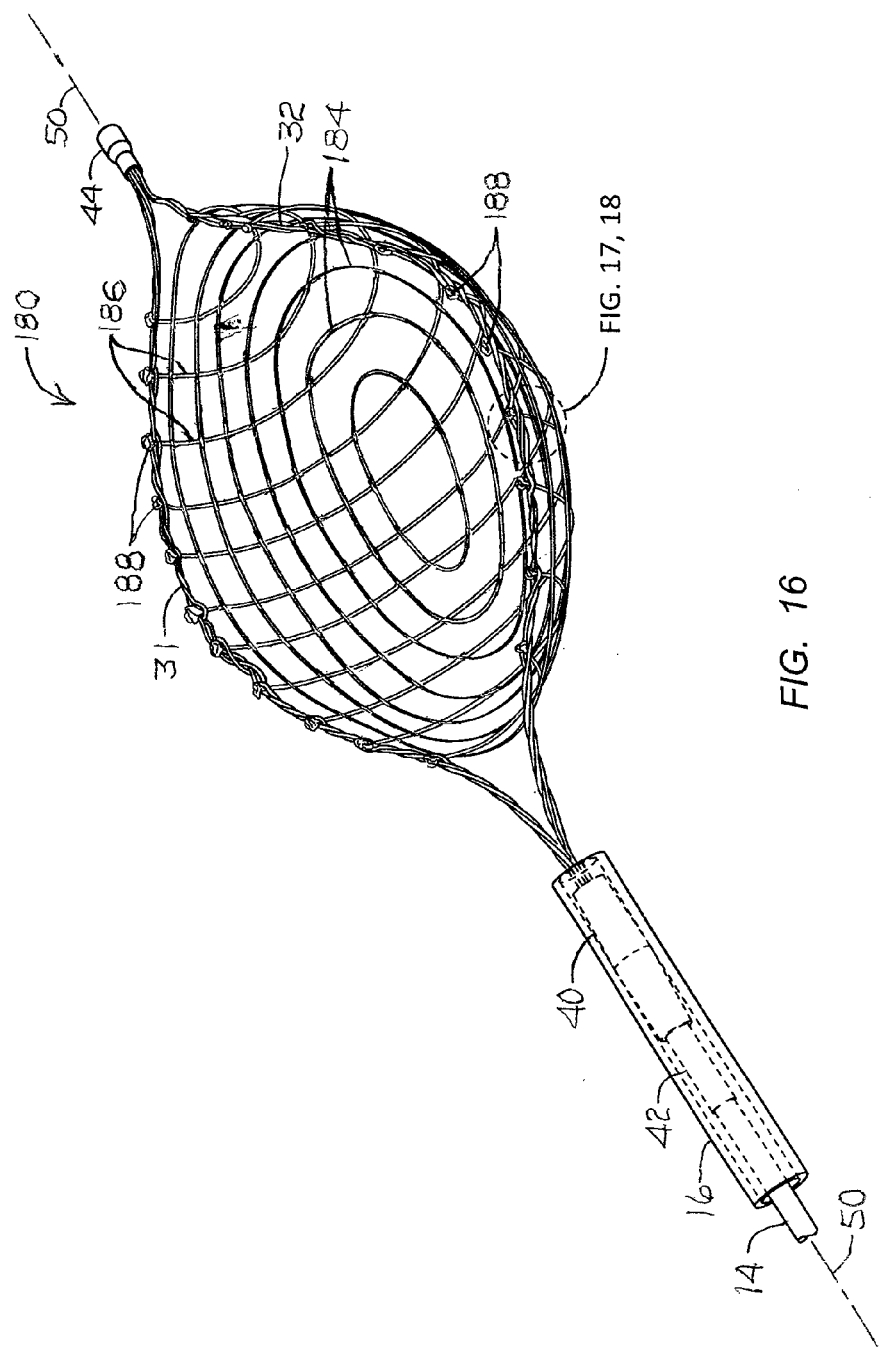
FIG. 16 is a perspective view from above of another example embodiment endoscopic retrieval device in which the basket portion comprises horizontal flexible thread loops suspended on a plurality of vertical suspension wires from the snare components that form the open mouth of the basket.

Another example embodiment retrieval device 180 shown diagrammatically in FIG. 16 has a somewhat different basket 182 than described in the examples above. The catheter 16, cable 14, proximal ferrule 40, distal ferrule 44, and snare wires 31, 32 are similar to those components shown and described above for the example retrieval device 10 in FIGS. 1-7, thus are given the same designator numbers for this example embodiment retrieval device 180. However, the basket 182, other than the snare wires 31, 32 is formed by a plurality of flexible thread loops 184 suspended in spaced apart relation to each other on a plurality of bowed wire strands 186, opposite ends of which are attached to the snare wires 31, 32, respectively. For example, the wire strands 186 can be poked through the thread loops 184, as shown diagrammatically in FIG. 17, and attached to the snare wires 31, 32 with knots 188 or any other suitable attachment instrumentality. Alternatively, the thread loops 184 can be attached in any other suitable manner to the wire strands 186, for example, with glue 189, as shown in FIG. 18.

The example retrieval device 180 functions similar to the example retrieval device 10 described above as it is extended from, or retracted back into, the catheter 16. Also, the example retrieval device 180 can be equipped with a surround material, similar to the surround material 162 in FIG. 13, or with a bag, similar to the bag 172 in FIG. 15, if desired.

Figure 19:
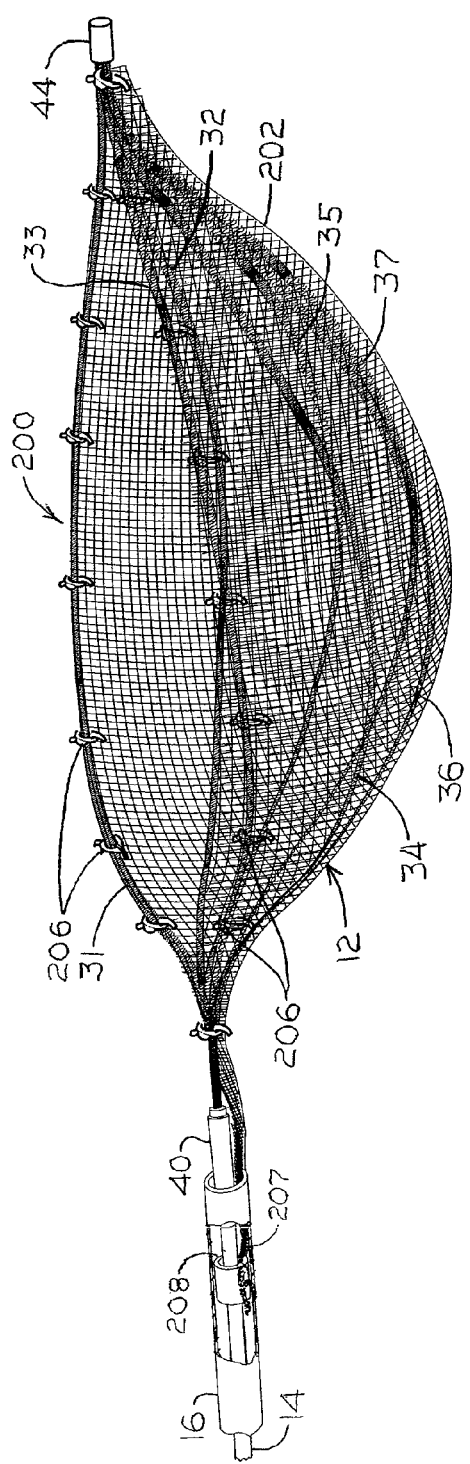
FIG. 19 is a perspective view of an example retrieval device similar to the example retrieval device in FIGS. 2-6 equipped with a net surround attached by ties to the rim or snare wires.

An example retrieval device 200 similar to the example retrieval device 10 in FIGS. 1-7 is shown diagrammatically in FIG. 19 equipped with a surround material 202 in lieu of the thread segments 60 in the example retrieval device 10. Since the retrieval device 200 in FIG. 19 is similar to the retrieval device 10 in FIGS. 1-7, similar components are numbered the same in FIG. 19 as in FIGS. 1-7. As shown in FIG. 19, the surround material 202 (shown as a net surround material in this example, but could be other materials) is mounted outside, but adjacent to, the basket frame wires 33, 34, 35, 36, 37 and attached to the rim or snare wires 31, 32 with ties 206, which extend through bits of the net surround 202 and are tied to the rim or snare wires 31, 32 in a manner such that the rim or snare wires 31, 32 and the basket frame wires 33, 34, 35, 36, 37, when extended in use mode, provide form to the surround material 202 in the shape of an open pocket.

Figure 20:
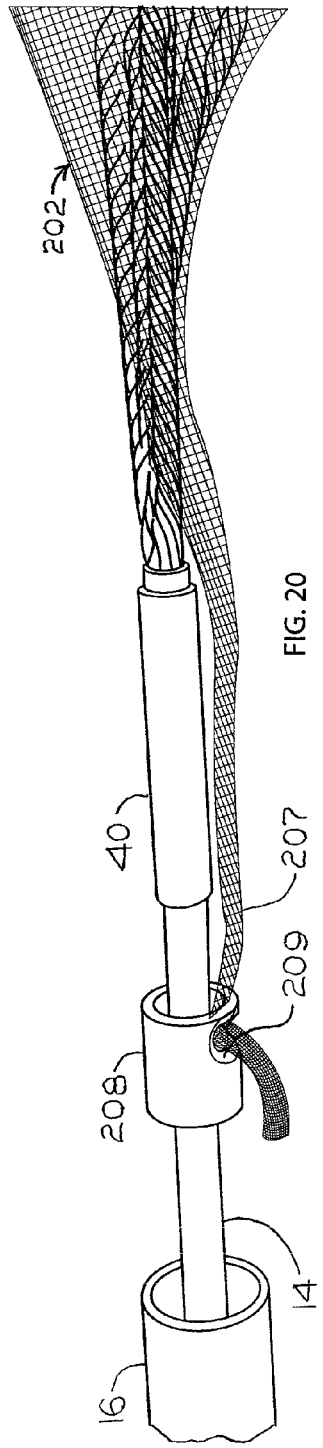
FIG. 20 is an enlarged perspective view of the connection of the proximal end of the net surround in FIG. 19 to the cable 14.

The proximal end 207 of the net surround 202 is terminated in a net ferrule 208, which is mounted on the cable 14 inwardly from the proximal ferrule 40 that attaches the proximal ends of the rim or snare wires 31, 32 and basket frame wires 33, 34, 35, 36, 37 to the cable 14, as best seen in FIGS. 19 and 20. Therefore, when the cable 14 draws the proximal ferrule 40 and wires 31, 32, 33, 34, 35, 36, 37 into the catheter 16, as described above, the proximal ferrule 40 contacts and pushes the net ferrule 208 longitudinally into the catheter 16, which pulls the net surround 202 into the catheter 16 along with the wires 31, 32, 33, 34, 35, 36, 37. On the other hand, when the cable 14 pushes the proximal ferrule 40 and wires 31, 32, 33, 34, 35, 36, 37 out of the catheter 16, the wires 31, 32, 33, 34, 35, 36, 37 pull the net surround 202 out of the catheter 16. As the wires 31, 32, 33, 34, 35, 36, 37 pull the net surround 202 out of the catheter 16, the proximal end 207 of the net surround 202 pulls the net ferrule 208 toward the front of the catheter 16 following the proximal ferrule 40.

As best seen in FIG. 20, with continuing reference to FIG. 19, the proximal end 207 of the net surround 202 is threaded into an open end of the net ferrule and out a lateral opening 209 in the net ferrule 208, which is sufficient to anchor the proximal end 207 of the net surround 208 to the net ferrule 208 by friction when the net ferrule 208 and proximal end 207 are positioned in the catheter 16. However, the proximal end 207 of the net surround 208 can be further secured to the net ferrule 208, if desired, for example, by a dollop of adhesive (not shown) or any other suitable securing instrumentality.

The example retrieval device 200' shown diagrammatically in FIG. 21 is pretty much the same as the example retrieval device 200 in FIGS. 19 and 20, except that the surround material 202 is attached to the rim or snare wires 31, 32 with laces 211, 212, instead of the ties 206. The laces 211, 212 are threaded back and forth through the surround material 202 and into and out of a plurality of eyes 64 in the rim or snare wires 31, 32, which are too small to show clearly in FIG. 21, but which can be seen, for example, in FIGS. 5, 6, 17, and 18.

The example retrieval device 220 shown diagrammatically in FIG. 22 is similar to the example retrieval device 11n with the smaller, narrowed mouth 130 in FIGS. 8 and 9, but it is shown diagrammatically in FIG. 22 equipped with a surround material 222 in lieu of the thread segments 60 in the example retrieval device 110. Since the retrieval device 220 in FIG. 22 is similar to the retrieval device 110 in FIGS. 8 and 9, similar components are numbered the same in FIG. 22 as in FIGS. 8 and 9. As shown in FIG. 22, the surround material 222 is mounted outside, but adjacent to, the basket frame wires 133, 134, 135, 136, 137 and attached to the rim or snare wires 131, 132 with ties 226, similar to the ties 206 in the example device 200 shown in FIG. 19 and described above. The surround material 222 could alternatively be attached to the rim or snare wires 131, 132 with laces, like the laces 211, 212 in the example device 200' in FIG. 21 or by any other suitable attachment instrumentality. The rim or snare wires 231, 232 and the basket frame wires 233, 234, 235, 236, 237, when extended in use mode, provide form to the net surround 222 in the shape of an open pocket. However, the surround material 222 closes and collapses when the basket 112 and surround material 222 are drawn by the cable 14 into the catheter 16.

The proximal end 227 of the surround material 222 is connected to a surround or net ferrule 228 (hereinafter surround ferrule 228 for simplicity) mounted on the cable 14 inside the catheter 16, as shown in FIG. 22, in a manner similar to the connection of the distal end 207 of the surround material 202 of the device 200 described above and shown in FIGS. 19 and 20. The surround ferrule 228 is mounted slidably on the cable 14 before the slidable ferrule 141 and proximal ferrule 140. Therefore, as the proximal ferrule 140 and rim or snare wires 131, 132 are pushed by the cable 14 out of the catheter 16 to deploy the basket 112, as described above for the example retrieval device 110 in FIGS. 8-10, the rim or snare wires 131, 132 pull the net surround 222 out of the catheter 16 along with the basket frame wires 133, 134, 135, 136, 137 until the mouth 130 and basket 119 are fully opened and extended. On the other hand, when the cable 14 pulls the proximal ferrule 140 and the rim or snare wires 131, 132 back into the catheter 16, the proximal ferrule 140 contacts and pushes the slidable ferrule 141 back into the catheter 16, which pulls the basket frame wires 233, 234, 235, 236, 237 back into the catheter 16, as described above for the example retrieval device 110 in FIGS. 8-12. Likewise, the slidable ferrule 141 then contacts and pushes the surround ferrule 228 farther back into the catheter 16, which pulls the surround material 222 back into the catheter 16 along with the basket frame wires 233, 234, 235, 236, 237 and the rim or snare wires 131, 132.

The surround ferrules 208, 228 in the example retrieval device embodiments 200, 220 described above are effective and convenient for attaching the proximal ends 207, 227 of the respective surrounds 202, 222 to the cable 14, but other attachment instrumentalities can also be used. For example, the proximal ends 202, 222 could be tied, stitched, or otherwise attached (not shown) to the cable 14, preferably, but not necessarily, at a location on the cable 14 where the proximal ferrule 40, 140 or the slidable ferrule 141 will bear on and pull the proximal end 207, 227 of the surround material 202, 222 into the catheter 16.

Figure 23:
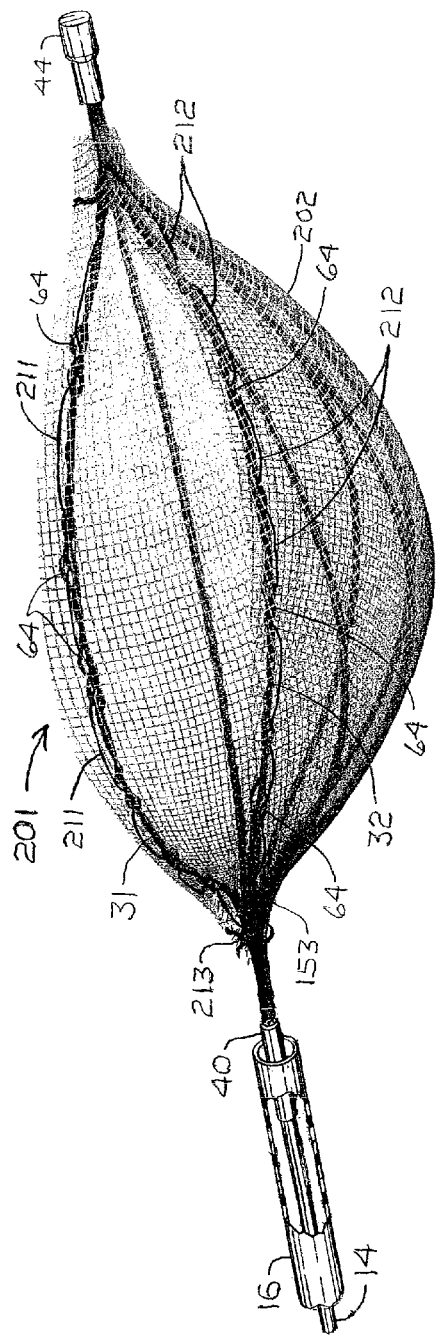
FIG. 23 is a perspective view of another example retrieval device similar to the example retrieval device in FIG. 21, but with the proximal end of the net surround truncated and fastened directly to the basket frame and snare wires.

Another example retrieval device embodiment 201 shown in FIG. 23 is a variation of the device embodiments 200' in FIG. 21 wherein the surround material 202 is fastened to the snare wires 31, 32 with laces 211, 212 as in the device embodiment 200' in FIG. 21, but the proximal end of the surround material 202 is truncated and fastened directly to the basket frame wires 33, 34, 35, 36, 37 and snare wires 31, 32 where they all join together for connection in the proximal ferrule 40. For example, the proximal ends of the laces 211, 212 are stitched through the proximal end of the surround 202 and tied together in a knot 213 around the gathered basket frame wires 33, 34, 35, 36, 37 and snare wires 31, 32 adjacent the bends 153 as shown in FIG. 23. Of course, persons skilled in the art will recognize that other means of attaching the proximal end of the surround 202 to the gathered basket frame wires 33, 34, 35, 36, 37 and snare wires 31, 32 could be used. For example, a band of metal, plastic, heat shrinkable material, or other material could be used to clamp or bind the proximal end of the net surround 202 to the gathered basket frame wires 33, 34, 35, 36, 37 and snare wires 31, 32. Also, a plurality of ties, such as the ties 206 in FIG. 19, or any other suitable fastener instrumentalities could be used instead of the laces 211, 212 for fastening the surround 202 to the snare wires 31, 32.

Figure 24:
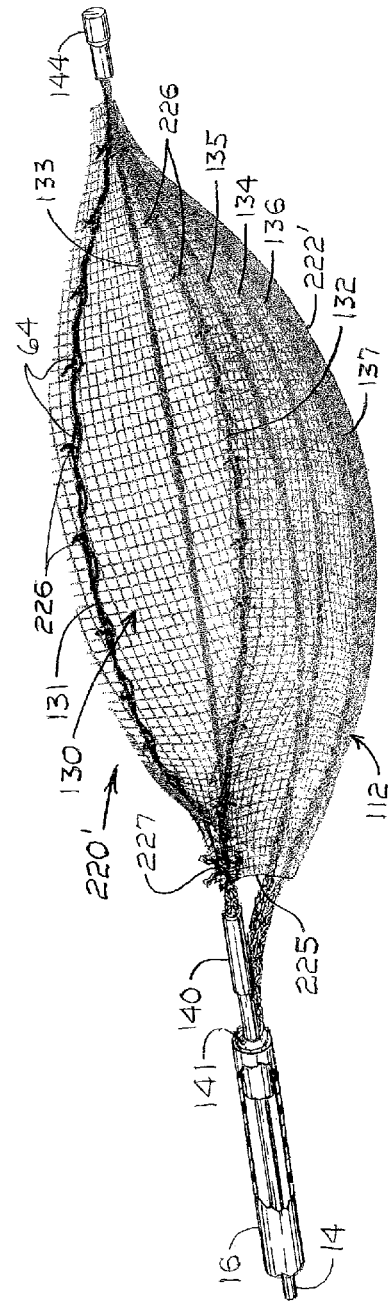
FIG. 24 is a perspective view of another example retrieval device similar to example retrieval device in FIG. 22, but with the proximal end of the net surround truncated and fastened directly to the snare wires.

Another example retrieval device embodiment 220' shown in FIG. 24 is similar to the example retrieval device embodiment 220 in FIG. 22, but with the proximal end of the surround material 222' truncated and fastened directly to the snare wires 131, 132 where they join together for connection to the proximal ferrule 140. For example, a tie 227 or any suitable alternative fastening, e.g., laces similar to those in FIG. 23, a band of metal, plastic, heat shrinkable material, or other material could be used to bind or clamp the proximal end of the surround 222' to the gathered snare wires 131, 132.

Another example alternate embodiment retrieval device 330 shown in FIG. 25 has an impermeable surround material 302 attached to the snare wires 31, 32 and extending around the basket frame wires 33, 34, 35, 36, 37 instead of the net surround 202 of the FIG. 23 example device 201. Such an impermeable surround material 302 may be useful, for example, in laproscopic procedures and other procedures in which it is desired to capture and retrieve fluids with or without particulate matter. The impermeable surround 302 can be attached to the snare wires 31, 32 with laces 311, 312, as shown in FIG. 24, similar to the lace attachments described above for the FIG. 23 example, or it can be attached with ties like the ties 226 in FIG. 22, or any other suitable attachment instrumentalities. The impermeable surround 302 can be made of thin plastic sheet or film material, for example, polyester (e.g., Mylar™, Terylene™, or others), cellophane, silk, polyethylene, polyamide, nylon, rayon, Teflon™, Dacron™, Kevlar™, liquid crystal polymer, or any of myriad other suitable materials. Such an impermeable surround can also be used instead of the net surrounds on any of the surgical retrieval device examples described above.

While all of the examples shown in FIGS. 1-25 are illustrated with a plurality of basket frame wires in addition to the two snare wires that form the mouth of the basket, for some applications and ease of assembly, only one frame wire in addition to the two snare wires may be sufficient. For example, another retrieval device embodiment 401 is shown in FIG. 26 with a structure similar to the example embodiment in FIG. 23, including two snare wires 31, 32 forming a mouth 404 of a basket 412, but the example basket 412 in FIG. 26 has only one additional frame wire 437 to provide a semi-rigid basket structure 412 to maintain the open pocket shape of the surround material 420. The frame wire snare wires 31, 32 and additional frame wire 437 can be made of the same materials and structural features, and they can be fastened together and to the cable 14 in the same manner as shown in FIG. 23, e.g., with a proximal ferrule 40 at one end and a distal ferrule 44 at the opposite end, although any of the snare wire and frame wire fastening and attachment techniques described above for the FIGS. 1-25 embodiments as well as other suitable fastening and mounting implementations or techniques can be used. The surround material 420, which is shown as a net or mesh surround material in FIG. 26, can be any of the surround materials described above and can be attached to the snare wires 31, 32 and/or to the cable 14 in any manner and with any of the instrumentalities described above for other embodiments. In the FIG. 26 example, the surround material is shown as being attached to the snare wires 31, 32 with a lace 422 similar to the lace attachment shown in FIG. 23. The lace 422 in this example is threaded through eyes 64 in the snare wires 31, 32, wrapped around the distal end of the basket 412 adjacent the distal ferrule 44 and tied at the proximal end of the basket 412 adjacent the proximal ferrule 40. The snare wires 31, 32 and frame wire 437 are collapsible and extendable in the same manner as described for any of the other example embodiments as the basket 412 is retracted into and extend out of the catheter 16. Of course more frame wires than the numbers of frame wires shown in FIGS. 1-26 could also be used if desired.

Figure 27:
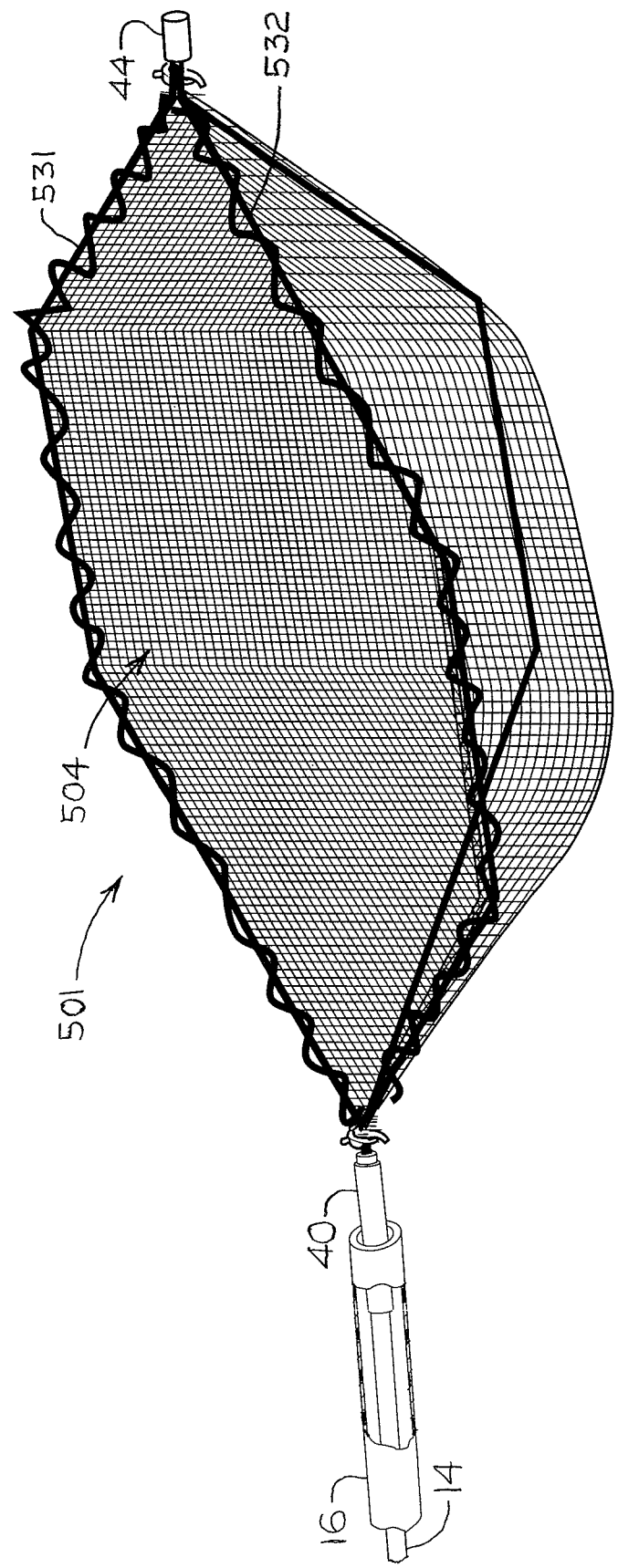
FIG. 27 is a perspective view of another example retrieval device showing snare wires and wire frame member bent to form a polygonal mouth and basket shape in the extended mode.

The snare wires and frame wires can also be bent or formed into different shapes or configurations than the smoothly curved shapes illustrated in the example FIGS. 1-26 embodiments. For example, as shown in FIG. 27, the retrieval device 501 has snare wires 531, 532 that are bent in a manner that forms a generally hexagonal-shaped mouth 504 when the basket 512 is extended out of the catheter 16. The example retrieval device embodiment 501 in FIG. 27 is shown with only one frame wire 537 in addition to the snare wires 531, 532, but any number of frame wires could be used. Also, the frame wire 537 is bent in a similar manner as the snare wires 531, 532 to form a semi-hexagonally shaped basket 512, but the frame wire 537 could be bent in another manner or just left to form the smoothly curved configuration of wire frame members shown in FIGS. 1-26. Also other bends to form other shaped mouths and/or baskets can be provided in the snare wires and/or frame wires as desired. For example, bends to form other polygonal shapes or other rounded shapes, such as a square, rectangular, or even crescent shaped mouth (not shown) can be provided.

The features, components, configurations, or attachments shown in FIGS. 1-27 can be used in various combinations with each other to form additional retrieval device embodiments, as will be understood by persons skilled in the art once they become familiar with the principles and advantages of the invention.

The foregoing description provides examples that illustrate the principles of the invention, which is defined by the features that follow. Since numerous insignificant modifications and changes will readily occur to those skilled in the art once they understand the invention, it is not desired to limit the invention to the exact example constructions and processes shown and described above. Accordingly, resort may be made to all suitable combinations, subcombinations, modifications, and equivalents that fall within the scope of the invention as defined by the features. The words "comprise," "comprises," "comprising," "include," "including," and "includes" when used in this specification, including the features, are intended to specify the presence of stated features, integers, components, or steps, but they do not preclude the presence or addition of one or more other features, integers, components, steps, or groups thereof. The terms upper, upwardly, lower, bottom, top, down, downwardly, vertical, horizontal, and other directional terms in this description are in reference to the diagrammatic orientations of the figures on the drawing sheets and are only used for convenience and clarity in this description unless otherwise indicated. The surgical retrieval device, including the example embodiments described above, can be used in any orientation.

The invention in which an exclusive property or privilege is claimed is defined as follows:

1. Surgical retrieval apparatus, comprising:
   a pair of bowed, resiliently deformable, wire snare members with bow shaped memory, each of said wire snare members having a proximal end and a distal end and said wire snare members being fastened together at their proximal ends in immovable relation to each other and to a distal end of a cable, said wire snare members extending longitudinally from their proximal ends in radially flared relation to each other to a common distal node where their distal ends are fastened together in immovable relation to each other; and at least one additional bowed, resiliently deformable, wire frame member with bow shaped memory between a proximal end and a distal end of the wire frame member, wherein the proximal end of the wire frame member is fastened to a slidable ferrule that is mounted in a slidable manner on the cable adjacent to the distal end of the cable such that the proximal end of the wire frame member is movable in relation to proximal ends of the wire snare member, and wherein the wire frame member extends from the slidable ferrule longitudinally to the common distal node where the distal end of the wire frame member is fastened together in immovable relation with the distal ends of the wire snare members such that the wire frame member in combination with the wire snare members form a collapsible basket configuration with the a mouth formed by the wire snare members.

2. The surgical retrieval apparatus of claim 1, wherein the wire frame member extends to the common distal node in radially flared formation at an angularly spaced position in relation to the wire snare members.

3. The surgical retrieval apparatus of claim 2, wherein a plurality of additional wire frame members extend from the slidable ferrule to the common distal node in radially flared formation at angularly spaced positions in relation to each other and to the wire snare members.

4. The surgical retrieval apparatus of claim 2, wherein the wire snare members and the wire frame members have distal ends that are fastened together at the distal node.

5. The surgical retrieval apparatus of claim 2, including a plurality of flexible thread segments extending transversely across the angular spaces between adjacent ones of the wire frame members and spaced longitudinally from each other.

6. The surgical retrieval apparatus of claim 1, including a surround material attached to the wire snare members and extending around the basket configuration that is formed by the wire frame member.

7. The surgical retrieval apparatus of claim 6, wherein the surround material is attached to the wire snare member with a plurality of ties.

8. The surgical retrieval apparatus of claim 6, wherein the surround material is attached to the wire snare member with laces that extend through eyelets in the wire snare wires.

9. The surgical retrieval apparatus of claim 6, wherein the surround material is a net.

10. The surgical retrieval apparatus of claim 6, wherein the surround material is an impermeable film.

11. Surgical retrieval apparatus, comprising:
a pair of bowed, resiliently deformable, wire snare members with bow shaped memory fastened together at their proximal ends in immovable relation to each other and to a distal end of a cable, said wire snare members extending longitudinally in radially flared relation to each other to a common distal node, wherein each one of the pair of wire snare members is formed with a plurality of wire strands twisted together in contact with each other such that a thread with a predetermined diameter cannot pass between any of the wire strands along a length of the snare wire between the proximal end and the distal node except at a plurality of locations positioned along said length in spaced apart relation to each other where one of the wire strands is spread apart from another of the wire strands to form eyes that accommodate lacing the thread through the eyes;

at least one additional bowed, resiliently deformable, wire frame member with bow shaped memory fastened at its proximal end in immovable relation to the distal end of the cable and extending longitudinally to the common distal node such that the at least one additional wire frame member forms a collapsible basket configuration with the a mouth formed by the wire snare members; and a surround material extending around the basket configuration that is formed by the at least one additional wire frame member, wherein marginal edge portions of the surround material are attached to the pair of wire snare members by the thread laced through the eyes and through the marginal edge portions of the surround material along said lengths of the wire snare members.

12. The surgical retrieval apparatus of claim 11, wherein the surround material is a net.

13. The surgical retrieval apparatus of claim 11, wherein the surround material is an impermeable film.

14. The surgical retrieval apparatus of claim 11, wherein a proximal end of the surround material is attached to the cable with a surround mounting ferrule that is mounted slideably on the cable.

15. The surgical retrieval apparatus of claim 11, wherein a proximal end of the surround material is fastened to the cable with a tie.

16. The surgical retrieval apparatus of claim 11, wherein the wire snare members are bent to form a desired bowed mouth shape.

17. The surgical retrieval apparatus of claim 11, wherein the bowed mouth shape is hexagonal.

18. The surgical retrieval apparatus of claim 11, wherein the surround material is sized for a snug fit with the at least one additional bowed, resiliently deformable, wire frame member.

19. The surgical retrieval apparatus of claim 11, wherein the surround material is sized to extend outwardly beyond the at least one additional bowed, resiliently deformable, wire frame member in the form of a bag.

20. Surgical retrieval apparatus, comprising:
a pair of bowed, resiliently deformable, wire snare members with bow shaped memory fastened together at their proximal ends in immovable relation to each other and to a distal end of a cable, said wire snare members extending longitudinally in radially flared relation to each other to a common distal node, wherein each one of the pair of wire snare members is formed with a plurality of wire strands twisted together in contact with each other such that ties with a predetermined diameter cannot pass between any of the wire strands along a length of the snare wire between the proximal end and the distal node except at a plurality of locations positioned along said length in spaced apart relation to each other where one of the wire strands is spread apart from another of the wire strands to form eyes that accommodate threading the ties through the eyes;

at least one additional bowed, resiliently deformable, wire frame member with bow shaped memory fastened at its proximal end in immovable relation to the distal end of the cable and extending longitudinally to the common distal node such that the at least one additional wire frame member forms a collapsible basket configuration with the a mouth formed by the wire snare members; and a surround material extending around the basket configuration that is formed by the at least one additional wire frame member, wherein marginal edge portions of the surround material are attached to the pair of wire snare members by a plurality of the ties that extend through the eyes and through bits of the marginal edge portions of the surround material along said lengths of the wire snare members.

* * * * *